US008637477B2

(12) United States Patent
George et al.

(10) Patent No.: US 8,637,477 B2
(45) Date of Patent: Jan. 28, 2014

(54) ANTIGENIC COMPOSITIONS AND USE OF SAME IN THE TARGETED DELIVERY OF NUCLEIC ACIDS

(75) Inventors: Rajan George, Edmonton (CA); Antoine Noujaim, Edmonton (CA); Bruce D. Hirsche, legal representative, Edmonton (CA)

(73) Assignee: Akshaya Bio Inc. (CA)

( * ) Notice: Subject to any disclaimer, the term of this patent is extended or adjusted under 35 U.S.C. 154(b) by 187 days.

(21) Appl. No.: 12/675,560

(22) PCT Filed: Aug. 29, 2008

(86) PCT No.: PCT/CA2008/001547
§ 371 (c)(1),
(2), (4) Date: Jan. 28, 2011

(87) PCT Pub. No.: WO2009/026723
PCT Pub. Date: Mar. 5, 2009

(65) Prior Publication Data
US 2011/0189180 A1 Aug. 4, 2011

Related U.S. Application Data

(60) Provisional application No. 60/968,978, filed on Aug. 30, 2007.

(51) Int. Cl.
*A61K 48/00* (2006.01)

(52) U.S. Cl.
USPC ........................................... 514/44; 536/24.5

(58) Field of Classification Search
None
See application file for complete search history.

(56) References Cited

U.S. PATENT DOCUMENTS

| 7,056,704 | B2 | 6/2006 | Tuschl et al. |
| 7,078,196 | B2 | 7/2006 | Tuschl et al. |
| 7,868,158 | B2 * | 1/2011 | Chen et al. ................... 536/24.5 |
| 2004/0001853 | A1 | 1/2004 | George et al. |
| 2005/0013828 | A1 | 1/2005 | George et al. |
| 2005/0031628 | A1 | 2/2005 | George et al. |
| 2006/0030003 | A1 | 2/2006 | Simon |

FOREIGN PATENT DOCUMENTS

| WO | WO 00/32625 | 6/2000 |
| WO | WO 2005/014838 | 2/2005 |
| WO | WO 2006/023491 | 3/2006 |

OTHER PUBLICATIONS

Autran et al. (Science 2004, vol. 305: 205-208).*
Berlyn et al., "Generation of CD4 and CD8 T Lymphocyte Responses by Dendritic Cells Armed with PSA/Anti-PSA (Antigen/Antibody) Complexes," Clinical Immunology, 2001, vol. 101(3), pp. 276-283.
Dykxhoorn et al., "The silent treatment: siRNAs as small molecule drugs," Gene Therapy, 2006, vol. 13, pp. 541-552.
Fire et al., "Potent and specific genetic interference by double-stranded RNA in Caenorhabditis elegans," Nature, 1998, vol. 391, pp. 806-811.
Hill et al., "Immune Modulation by Silencing IL-12 Production in Dendritic Cells Using Small Interfering RNA," The Journal of Immunology, 2003, vol. 171, pp. 691-696.
Shen et al., "Silencing of SOCS1 enhances antigen presentation by dendritic cells and antigen-specific anti-tumor immunity," Nature Biotechnology, 2004, vol. 22(12), pp. 1546-1553.
Song et al., "An Alternative and Effective HIV Vaccination Approach Based on Inhibition of Antigen Presentation Attenuators in Dendritic Cells," PLoS Medicine, 2006, vol. 3(1), 18 pages.
Song et al., "Antibody mediated in vivo delivery of small interfering RNAs via cell-surface receptors," Nature Biotechnology, 2005, vol. 23(6), pp. 709-717.
Yoshimura et al., "SOCS proteins, cytokine signalling and immune regulation," Nature Reviews Immunology, 2007, vol. 7, pp. 454-465.
International Search Report for International (PCT) Application No. PCT/CA2008/0015747, mailed Nov. 20, 2008.
Written Opinion for International (PCT) Patent Application No. PCT/CA2008/0015747, mailed Nov. 20, 2008.
International Preliminary Report on Patentability for International (PCT) Patent Application No. PCT/CA2008/0015747, mailed Mar. 2, 2010.
Brandenburg et al., "A Novel System for Efficient Gene Transfer Into Primary Human Hepatocytes Via Cell-Permeable Hepatitis B Virus-like Particle," Hepatology, 2005, vol. 42, No. 6, pp. 1300-1309.
Cooper et al., "Clathrin-mediated Endocytosis and Lysosomal Cleavage of Hepatitis B Virus Capsid-like Core Particles," Journal of Biological Chemistry, 2006, vol. 281, No. 24, pp. 16563-16569.
Cooper et al., "Recombination Viral Capsids as an Efficient Vehicle of Oligonucleotide Delivery Into Cells," Biochemical and Biophysical Research Communications, 2005, vol. 327, Iss. 4, pp. 1094-1099.
Storni et al., "Nonmethylated CG Motifs Packaged into Virus-Like Particles Induce Protective Cytotoxic T Cell Responses in the Absence of Systemic Side Effects," The Journal of Immunology, 2004, vol. 172, No. 3, pp. 1777-1785.
Wen et al. "Targeted Inhibition of HBV Gene Expression by Single-Chain Antibody Mediated Small Interfering RNA Delivery," Hepatology, 2007, vol. 46, No. 1, pp. 84-94.

* cited by examiner

*Primary Examiner* — Kimberly Chong
(74) *Attorney, Agent, or Firm* — Sheridan Ross P.C.

(57) ABSTRACT

Methods and compositions are provided for delivery of therapeutic nucleic acids to a target cell. A chimeric antigen is provided to encapsulate, bind, or otherwise carry a nucleic acid molecule to a target cell where the chimeric antigen and nucleic acid are internalized by receptor-mediated endocytosis. The chimeric antigen has a nucleic acid interaction domain, a target binding domain, and an immune response domain that may include a target antigen. Targeting is generally provided by the specificity of the target binding domain for a particular target cell receptor, but may also be provided by inclusion of a targeting antigen within the immune response domain. The combined delivery of chimeric antigen and nucleic acid, which may be a siRNA, may be synergistic in certain applications, for example in breaking host tolerance to a virus or in

Figure 2b Nucleotide and amino acid sequence of HBV Core Protein

```
1/1                                     31/11
GAC ATT GAC CCT TAT AAA GAA TTT GGA GCT ACT GTG GAG TTA CTC TCG TTT TTG CCT TCT
 D   I   D   P   Y   K   E   F   G   A   T   V   E   L   L   S   F   L   P   S
61/21                                   91/31
GAC TTC TTT CCT TCC GTC AGA GAT CTC CTA GAC ACC GCC TCG GCT CTG TAT CGG GAA GCC
 D   F   F   P   S   V   R   D   L   L   D   T   A   S   A   L   Y   R   E   A
121/41                                  151/51
TTA CAG TCT CCT GAG CAT TGC TCA CCT CAC CAT ACC GCA CTC AGG CAA GCC ATT CTC TGC
 L   Q   S   P   E   H   C   S   P   H   H   T   A   L   R   Q   A   I   L   C
181/61                                  211/71
TGG GGG GAA TTG ATG ACT CTA GCT ACC TGG GTG GGT AAT AAT TTG GAA GAT CCA GCA TCC
 W   G   E   L   M   T   L   A   T   W   V   G   N   N   L   E   D   P   A   S
241/81                                  271/91
AGG GAT CTA GTA GTC AAT TAT GTT AAT ACT AAC ATG GGA TTA AAG ATC AGG CAA CTC TTG
 R   D   L   V   V   N   Y   V   N   T   N   M   G   L   K   I   R   Q   L   L
301/101                                 331/111
TGG TTT CAT ATC TCT TGC CTT ACT TTT GGA AGA GAA ACT GTA CTT GAA TAT TTG GTC TCT
 W   F   H   I   S   C   L   T   F   G   R   E   T   V   L   E   Y   L   V   S
361/121                                 391/131
TTC GGA GTG TGG ATT CGC ACT CCT CCA GCC TAT AGA CCA CCA AAT GCC CCT ATC TTA TCA
 F   G   V   W   I   R   T   P   P   A   Y   R   P   P   N   A   P   I   L   S
421/141                                 451/151
ACA CTT CCG GAA ACT ACT GTT GTT AGA CGA CGG GAC CGA GGC AGG TCC CCT AGA AGA AGA
 T   L   P   E   T   T   V   V   R   R   R   D   R   G   R   S   P   R   R   R
481/161                                 511/171
ACT CCC TCG CCT CGC AGA CGC AGA TCT CAA TCG CCG CGT CGC AGA AGA TCT CAA TCT CGG
 T   P   S   P   R   R   R   S   Q   S   P   R   R   R   S   Q   S   R
541/181                                 571/191
GAA TCT CAA TGT TCG CGG CCG CTT TCG AAT CTA GAG CCT GCA GTC TCG AGG CAT GCG GTA
 E   S   Q   C   S   R   P   L   S   N   L   E   P   A   V   S   R   H   A   V
```

Figure 3d-Chimigen® NS5A – Protamine Tail Vaccine

```
1/1                                     31/11
ATG GTA AGC GCT ATT GTT TTA TAT GTG CTT TTG GCG GCG GCG GCG CAT TCT GCC TTT GCG
 M   V   S   A   I   V   L   Y   V   L   L   A   A   A   A   H   S   A   F   A
61/21                                   91/31
TAT CTG CAG GTA CGG TCC GAA ACC ATG TCG TAC TAC CAT CAC CAT CAC CAT CAC GAT TAC
 Y   L   Q   V   R   S   E   T   M   S   Y   Y   H   H   H   H   H   H   D   Y
121/41                                  151/51
GAT ATC CCA ACG ACC GAA AAC CTG TAT TTT CAG GGC GCC ATG GAT CCG GAA TTC TCC GGT
 D   I   P   T   T   E   N   L   Y   F   Q   G   A   M   D   P   E   F   S   G
181/61                                  211/71
TCC TGG CTA AGG GAC ATC TGG GAC TGG ATA TGC GAG GTG CTG AGC GAC TTT AAG ACC TGG
 S   W   L   R   D   I   W   D   W   I   C   E   V   L   S   D   F   K   T   W
241/81                                  271/91
CTG AAA GCC AAG CTC ATG CCA CAA CTG CCT GGG ATT CCC TTT GTG TCC TGC CAG CGC GGG
 L   K   A   K   L   M   P   Q   L   P   G   I   P   F   V   S   C   Q   R   G
301/101                                 331/111
TAT AGG GGG GTC TGG CGA GGA GAC GGC ATT ATG CAC ACT CGC TGC CAC TGT GGA GCT GAG
 Y   R   G   V   W   R   G   D   G   I   M   H   T   R   C   H   C   G   A   E
361/121                                 391/131
ATC ACT GGA CAT GTC AAA AAC GGG ACG ATG AGG ATC GTC GGT CCT AGG ACC TGC AGG AAC
 I   T   G   H   V   K   N   G   T   M   R   I   V   G   P   R   T   C   R   N
421/141                                 451/151
ATG TGG AGT GGG ACG TTC CCC ATT AAC GCC TAC ACC ACG GGC CCC TGT ACT CCC CTT CCT
 M   W   S   G   T   F   P   I   N   A   Y   T   T   G   P   C   T   P   L   P
481/161                                 511/171
GCG CCC AAC TAT AAG TTC GCG CTG TGG AGG GTG TCT GCA GAG GAA TAC GTG GAG ATA AGG
 A   P   N   Y   K   F   A   L   W   R   V   S   A   E   E   Y   V   E   I   R
541/181                                 571/191
CGG GTG GGG GAC TTC CAC TAC GTA TCG GGT ATG ACT ACT GAC AAT CTT AAA TGC CCG TGC
 R   V   G   D   F   H   Y   V   S   G   M   T   T   D   N   L   K   C   P   C
601/201                                 631/211
CAG ATC CCA TCG CCC GAA TTT TTC ACA GAA TTG GAC GGG GTG CGC CTA CAC AGG TTT GCG
 Q   I   P   S   P   E   F   F   T   E   L   D   G   V   R   L   H   R   F   A
661/221                                 691/231
CCC CCT TGC AAG CCC TTG CTG CGG GAG GAG GTA TCA TTC AGA GTA GGA CTC CAC GAG TAC
 P   P   C   K   P   L   L   R   E   E   V   S   F   R   V   G   L   H   E   Y
721/241                                 751/251
CCG GTG GGG TCG CAA TTA CCT TGC GAG CCC GAA CCG GAC GTA GCC GTG TTG ACG TCC ATG
 P   V   G   S   Q   L   P   C   E   P   E   P   D   V   A   V   L   T   S   M
781/261                                 811/271
CTC ACT GAT CCC TCC CAT ATA ACA GCA GAG GCG GCC GGG AGA AGG TTG GCG AGA GGG TCA
 L   T   D   P   S   H   I   T   A   E   A   A   G   R   R   L   A   R   G   S
841/281                                 871/291
CCC CCT TCT ATG GCC AGC TCC TCG GCT AGC CAG CTG TCC GCT CCA TCT CTC AAG GCA ACT
 P   P   S   M   A   S   S   S   A   S   Q   L   S   A   P   S   L   K   A   T
901/301                                 931/311
TGC ACC GCC AAC CAT GAC TCC CCT GAC GCC GAG CTC ATA GAG GCT AAC CTC CTG TGG AGG
 C   T   A   N   H   D   S   P   D   A   E   L   I   E   A   N   L   L   W   R
961/321                                 991/331
CAG GAG ATG GGC GGC AAC ATC ACC AGG GTT GAG TCA GAG AAC AAA GTG GTG ATT CTG GAC
 Q   E   M   G   G   N   I   T   R   V   E   S   E   N   K   V   V   I   L   D
1021/341                                1051/351
TCC TTC GAT CCG CTT GTG GCA GAG GAG GAT GAG CGG GAG GTC TCC GTA CCT GCA GAA ATT
 S   F   D   P   L   V   A   E   E   D   E   R   E   V   S   V   P   A   E   I
1081/361                                1111/371
CTG CGG AAG TCT CGG AGA TTC GCC CGG GCC CTG CCC GTC TGG GCG CGG CCG GAC TAC AAC
 L   R   K   S   R   R   F   A   R   A   L   P   V   W   A   R   P   D   Y   N
1141/381                                1171/391
CCC CCG CTA GTA GAG ACG TGG AAA AAG CCT GAC TAC GAA CCA CCT GTG GTC CAT GGC TGC
 P   P   L   V   E   T   W   K   K   P   D   Y   E   P   P   V   V   H   G   C
``` continuation of Figure 3d

```
1201/401                                        1231/411
CCG CTA CCA CCT CCA CGG TCC CCT CCT GTG CCT CCG CCT CGG AAA AAG CGT ACG GTG GTC
 P   L   P   P   P   R   S   P   P   V   P   P   P   R   K   K   R   T   V   V
1261/421                                        1291/431
CTC ACC GAA TCA ACC CTA TCT ACT GCC TTG GCC GAG CTT GCC ACC AAA AGT TTT GGC AGC
 L   T   E   S   T   L   S   T   A   L   A   E   L   A   T   K   S   F   G   S
1321/441                                        1351/451
TCC TCA ACT TCC GGC ATT ACG GGC GAC AAT ACG ACA ACA TCC TCT GAG CCC CCC CCT TCT
 S   S   T   S   G   I   T   G   D   N   T   T   T   S   S   E   P   A   P   S
1381/461                                        1411/471
GGC TGC CCC CCC GAC TCC GAC GTT GAG TCC TAT TCT TCC ATG CCC CCC CTG GAG GGG GAG
 G   C   P   P   D   S   D   V   E   S   Y   S   S   M   P   P   L   E   G   E
1441/481                                        1471/491
CCT GGC GAT CCG GAT CTC AGC GAC GGG TCA TGG TCG ACG GTC AGT AGT GGG GCC GAC ACG
 P   G   D   P   D   L   S   D   G   S   W   S   T   V   S   S   G   A   D   T
1501/501                                        1531/511
GAA GAT GTC GTG TGC GGA CTA GTG CGG CCG CAA GGC GGC GGA TCC GTG GAC AAG AAA ATT
 E   D   V   V   C   G   L   V   R   P   Q   G   G   G   S   V   D   K   K   I
1561/521                                        1591/531
GTG CCC AGG GAT TGT GGT TGT AAG CCT TGC ATA TGT ACA GTC CCA GAA GTA TCA TCT GTC
 V   P   R   D   C   G   C   K   P   C   I   C   T   V   P   E   V   S   S   V
1621/541                                        1651/551
TTC ATC TTC CCC CCA AAG CCC AAG GAT GTG CTC ACC ATT ACT CTC ACT CCT AAG GTC ACG
 F   I   F   P   P   K   P   K   D   V   L   T   I   T   L   T   P   K   V   T
1681/561                                        1711/571
TGT GTT GTG GTA GAC ATC AGC AAG GAT GAT CCC GAG GTC CAG TTC AGC TGG TTT GTA GAT
 C   V   V   V   D   I   S   K   D   D   P   E   V   Q   F   S   W   F   V   D
1741/581                                        1771/591
GAT GTG GAG GTG CAC ACA GCT CAG ACG CAA CCC CGG GAG GAG CAG TTC AAC AGC ACT TTC
 D   V   E   V   H   T   A   Q   T   Q   P   R   E   E   Q   F   N   S   T   F
1801/601                                        1831/611
CGC TCA GTC AGT GAA CTT CCC ATC ATG CAC CAG GAC TGG CTC AAT GGC AAG GAG TTC AAA
 R   S   V   S   E   L   P   I   M   H   Q   D   W   L   N   G   K   E   F   K
1861/621                                        1891/631
TGC AGG GTC AAC AGT GCA GCT TTC CCT GCC CCC ATC GAG AAA ACC ATC TCC AAA ACC AAA
 C   R   V   N   S   A   A   F   P   A   P   I   E   K   T   I   S   K   T   K
1921/641                                        1951/651
GGC ACA CCC AAG GCT CCA CAG GTG TAC ACC ATT CCA CCT CCC AAG GAG CAG ATG GCC AAG
 G   R   P   K   A   P   Q   V   Y   T   I   P   P   P   K   E   Q   M   A   K
1981/661                                        2011/671
GAT AAA GTC AGT CTG ACC TGC ATG ATA ACA GAC TTC TTC CCT GAA GAC ATT ACT GTG GAG
 D   K   V   S   L   T   C   M   I   T   D   F   F   P   E   D   I   T   V   E
2041/681                                        2071/691
TGG CAG TGG AAT GGG CAG CCA GCG GAG AAC TAC AAG AAC ACT CAG CCC ATC ATG GAC ACA
 W   Q   W   N   G   Q   P   A   E   N   Y   K   N   T   Q   P   I   M   D   T
2101/701                                        2131/711
GAT GGC TCT TAC TTC GTC TAC AGC AAG CTC AAT GTG CAG AAG AGC AAC TGG GAG GCA GGA
 D   G   S   Y   F   V   Y   S   K   L   N   V   Q   K   S   N   W   E   A   G
2161/721                                        2191/731
AAT ACT TTC ACC TGC TCT GTG TTA CAT GAG GGC CTG CAC AAC CAC CAT ACT GAG AAG AGC
 N   T   F   T   C   S   V   L   H   E   G   L   H   N   H   H   T   E   K   S
2221/741                                        2251/751
CTC TCC CAC TCT CCT GGG CTG AAT CTA GAG GAA ACT ACT GTT GTT AGA CGA CGG GAC CGA
 L   S   H   S   P   G   L   N   L   E   E   T   T   V   V   R   R   R   D   R
2281/761                                        2311/771
GGC AGG TCC CCT AGA AGA AGA ACT CCC TCG CCT CGC AGA CGC AGA TCT CAA TCG CCC CGT
 G   R   S   P   R   R   R   T   P   S   P   R   R   R   S   Q   S   P   R
2341/781                                        2371/791
CGC AGA AGA TCT CAA TCT CGG GAA TCT CAA TGT CAA AGC TTG TCG AGA AGT ACT AGA GGA
 R   R   R   S   Q   S   R   E   S   Q   C   Q   S   L   S   R   S   T   R   G
2401/801
TCA TAA
 S   *
```

Figure 4b: Chimigen® HBV Multi-antigen (S1/S2-Core) Vaccine

```
1/1                                        31/11
ATG GTA AGC GCT ATT GTT TTA TAT GTG CTT    TTG GCG GCG GCG GCG CAT TCT GCC TTT GCG
 M   V   S   A   I   V   L   Y   V   L      L   A   A   A   A   H   S   A   F   A
61/21                                      91/31
TAT CTG CAG GTA CGG TCC GAA ACC ATG TCG    TAC TAC CAT CAC CAT CAC CAT CAC GAT TAC
 Y   L   Q   V   R   S   E   T   M   S      Y   Y   H   H   H   H   H   H   D   Y
121/41                                     151/51
GAT ATC CCA ACG ACC GAA AAC CTG TAT TTT    CAG GGC GCC ATG GAT CCG GAA TTC AAA GGC
 D   I   P   T   T   E   N   L   Y   F      Q   G   A   M   D   P   E   F   K   G
181/61                                     211/71
CTA CGT CGA CGA ATG AAA AAA TGG TCA TCA    AAA CCT CGC AAA GGC ATG GGA ACG AAT CTT
 L   R   R   R   M   K   K   W   S   S      K   P   R   K   G   M   G   T   N   L
181/61                                     211/71
TCT GTT CCC AAC CCT CTG GGA TTC TTT CCC    GAT CAT CAG TTG GAC CCT GTA TTC GGA GCC
 S   V   P   N   P   L   G   F   F   P      D   H   Q   L   D   P   V   F   G   A
241/81                                     271/91
AAC TCA AAC AAT CCA GAT TGG GAC TTC AAC    CCC ATC AAG GAC CAC TGG CCA GCA GCC AAC
 N   S   N   N   P   D   W   D   F   N      P   I   K   D   H   W   P   A   A   N
301/101                                    331/111
CAG GTA GGA GTG GGA GCA TTC GGG CCA GGG    TTC ACC CCT CCA CAC GGC GGT GTT TTG GGG
 Q   V   G   V   G   A   F   G   P   G      F   T   P   P   H   G   G   V   L   G
361/121                                    391/131
TGG AGC CCT CAG GCT CAG GGC ATG TTG ACC    CCA GTG TCA ACA ATT CCT CCT CCT GCC TCC
 W   S   P   Q   A   Q   G   M   L   T      P   V   S   T   I   P   P   P   A   S
421/141                                    451/151
GCC AAT CGG CAG TCA GGA AGG CAG CCT ACT    CCC ATC TCT CCA CCT CTA AGA GAC AGT CAT
 A   N   R   Q   S   G   R   Q   P   T      P   I   S   P   P   L   R   D   S   H
481/161                                    511/171
CCT CAG GCC ATG CAG TGG AAT TCC ACT GCC    TTC CAC CAA GCT CTG CAA GAC CCC AGA GTC
 P   Q   A   M   Q   W   N   S   T   A      F   H   Q   A   L   Q   D   P   R   V
541/181                                    571/191
AGG GGT CTG TAT TTC CCT GCT GGT GGC TCC    AGT TCA GGA ACA GTA AAC CCT GCT CCG AAT
 R   G   L   Y   F   P   A   G   G   S      S   S   G   T   V   N   P   A   P   N
601/201                                    631/211
ATT GCC TCT CAC ATC TCG TCA ATC TCC GCG    ACG ACC GGG GAC CCT GTG ACG AAC ATG GAC
 I   A   S   H   I   S   S   I   S   A      R   T   G   D   P   V   T   N   M   D
661/221                                    691/231
ATT GAC CCT TAT AAA GAA TTT GGA GCT ACT    GTG GAG TTA CTC TCG TTT TTG CCT TCT GAC
 I   D   P   Y   K   E   F   G   A   T      V   E   L   L   S   F   L   P   S   D
721/241                                    751/251
TTC TTT CCT TCC GTC AGA GAT CTC CTA GAC    ACC GCC TCG GCT CTG TAT CGG GAA GCC TTA
 F   F   P   S   V   R   D   L   L   D      T   A   S   A   L   Y   R   E   A   L
781/261                                    811/271
GAG TCT CCT GAG CAT TGC TCA CCT CAC CAT    ACC GCA CTC AGG CAA GCA ATT CTC TGC TGG
 E   S   P   E   H   C   S   P   H   H      T   A   L   R   Q   A   I   L   C   W
841/281                                    871/291
GGG GAA TTG ATG ACT CTA GCT ACC TGG GTG    GGT AAT AAT TTG GAA GAT CCA GCA TCC AGG
 G   E   L   M   T   L   A   T   W   V      G   N   N   L   E   D   P   A   S   R
901/301                                    931/311
GAT CTA GTA GTC AAT TAT GTT AAT ACT AAC    ATG GGA TTA AAG ATC AGG CAA CTC TTG TGG
 D   L   V   V   N   Y   V   N   T   N      M   G   L   K   I   R   Q   L   L   W
961/321                                    991/331
TTT CAT ATC TCT TGC CTT ACT TTT GGA AGA    GAA ACT GTA CTT GAA TAT TTG GTC TCT TTC
 F   H   I   S   C   L   T   F   G   R      E   T   V   L   E   Y   L   V   S   F
1021/341                                   1051/351
GGA GTG TGG ATT CGC ACT CCT CCA GCC TAT    AGA CCA CCA AAT GCC CCT ATC TTA TCA ACA
 G   V   W   I   R   T   P   P   A   Y      R   P   P   N   A   P   I   L   S   T
1081/361                                   1111/371
CTT CCG GAA ACT ACT GTT GTT AGA CGA CGG    GAC CGA GGC AGG TCC CCT AGA AGA AGA ACT
 L   P   E   T   T   V   V   R   R   R      D   R   G   R   S   P   R   R   R   T
``` continuation of Figure 4b

```
1141/381                                      1171/391
CCC TCG CCT CGC AGA CGC AGA TCT CAA TCG       CCG CGT CGC AGA AGA TCT CAA TCT CGG GAA
 P   S   P   R   R   R   R   S   Q   S        P   R   R   R   R   S   Q   S   R   E
1201/401                                      1231/411
TCT CAA TGT GTG CGG CCG CAA GGC GGC GGA       TCC GTG GAC AAG AAA ATT GTG CCC GCG GAT
 S   Q   C   V   R   P   Q   G   G   G        S   V   D   K   K   I   V   P   A   D
1261/421                                      1291/431
TGT GGT TGT GCG CCT TGC ATA TGT GCA GTC       CCA GAA GTA TCA TCT GTC TTC ATC TTC CCC
 C   G   C   A   P   C   I   C   A   V        P   E   V   S   S   V   F   I   F   P
1321/441                                      1351/451
CCA AAG CCC AAG GAT GTG CTC ACC ATT ACT       CTG ACT CCT AAG GTC ACG TGT GTT GTG GTA
 P   K   P   K   D   V   L   T   I   T        L   T   P   K   V   T   C   V   V   V
1381/461                                      1411/471
GAC ATC AGC AAG GAT GAT CCC GAG GTC CAG       TTC AGC TGG TTT GTA GAT GAT GTG GAG GTG
 D   I   S   K   D   D   P   E   V   Q        F   S   W   F   V   D   D   V   E   V
1441/481                                      1471/491
CAC ACA GCT CAG ACG CAA CCC CGG GAG GAG       CAG TTC AAC AGC ACT TTC CGC TCA GTC AGT
 H   T   A   Q   T   Q   P   R   E   E        Q   F   N   S   T   F   R   S   V   S
1501/501                                      1531/511
GAA CTT CCC ATC ATG CAC CAG GAC TGG CTC       AAT GGC AAG GAG TTC AAA TGC AGG GTC AAC
 E   L   P   I   M   H   Q   D   W   L        N   G   K   E   F   K   C   R   V   N
1561/521                                      1591/531
AGT GCA GCT TTC CCT GCC CCC ATC GAG AAA       ACC ATC TCC AAA ACC AAA GGC AGA CCG AAG
 S   A   A   F   P   A   P   I   E   K        T   I   S   K   T   K   G   R   P   K
1621/541                                      1651/551
GCT CCA CAG GTG TAC ACC ATT CCA CCT CCC       AAG GAG CAG ATG GCC AAG GAT AAA GTC AGT
 A   P   Q   V   Y   T   I   P   P   P        K   E   Q   M   A   K   D   K   V   S
1691/561                                      1711/571
CTG ACC TGC ATG ATA ACA GAC TTC TTC CCT       GAA GAC ATT ACT GTG GAG TGG CAG TGG AAT
 L   T   C   M   I   T   D   F   F   P        E   D   I   T   V   E   W   Q   W   N
1741/581                                      1771/591
GGG CAG CCA GCG GAG AAC TAC AAG AAC ACT       CAG CCC ATC ATG GAC ACA GAT GGC TCT TAC
 G   Q   P   A   E   N   Y   K   N   T        Q   P   I   M   D   T   D   G   S   Y
1801/601                                      1831/611
TTC GTC TAC AGC AAG CTC AAT GTG CAG AAG       AGC AAC TGG GAG GCA GGA AAT ACT TTC ACC
 F   V   Y   S   K   L   N   V   Q   K        S   N   W   E   A   G   N   T   F   T
1861/621                                      1891/631
TGC TCT GTG TTA CAT GAG GGC CTG CAC AAC       CAC CAT ACT GAG AAG AGC CTC TCC CAC TCT
 C   S   V   L   H   E   G   L   H   N        H   H   T   E   K   S   L   S   H   S
1921/641                                      1951/651
CCT GGG CTG CAA AGC TTG TCG AGA AGT ACT       AGA GGA TCA TAA
 P   G   L   Q   S   L   S   R   S   T        R   G   S   *
```

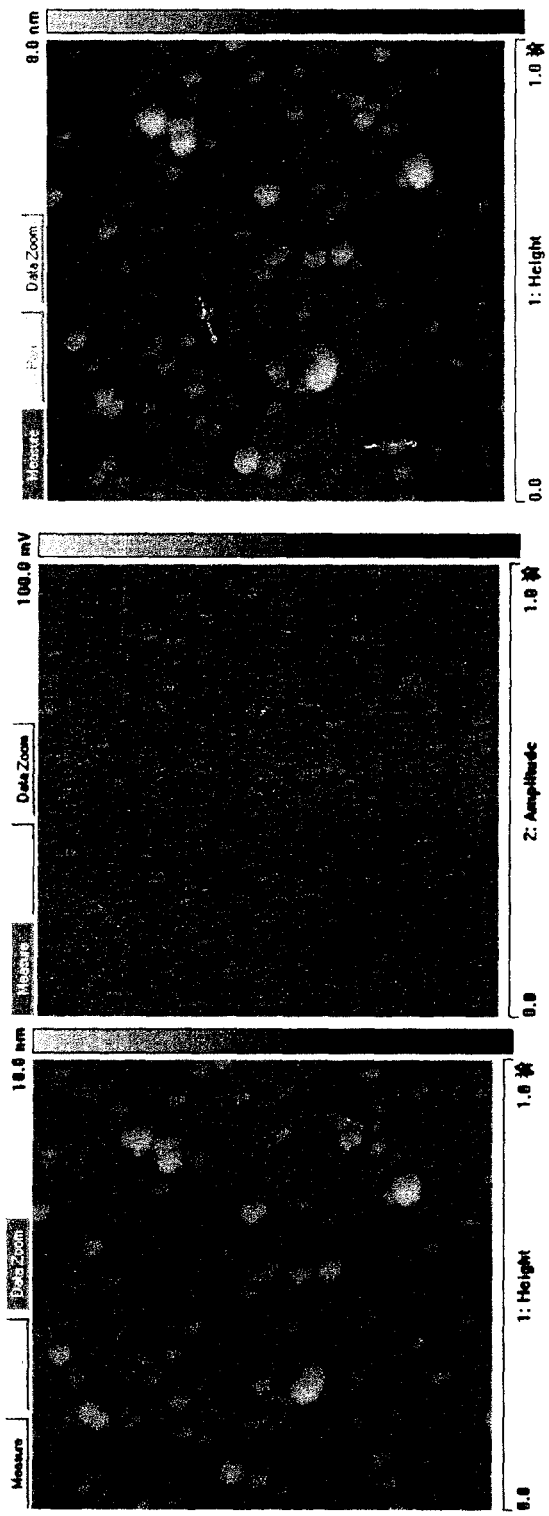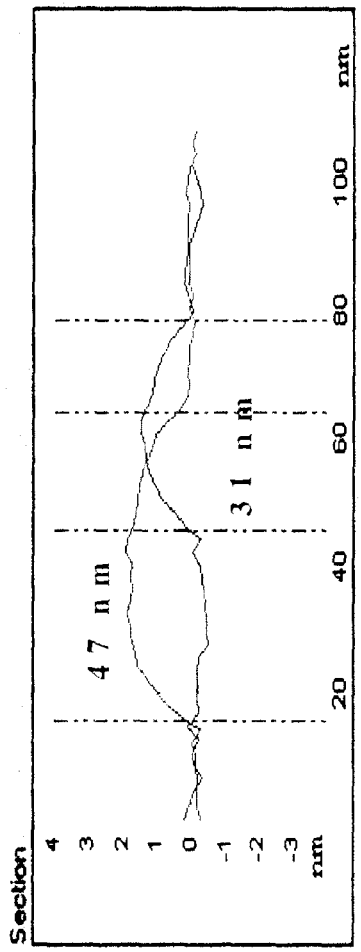
Fig 7a  Fig 7b  Fig 7c  Fig 7d

Two stimulations

One stimulation

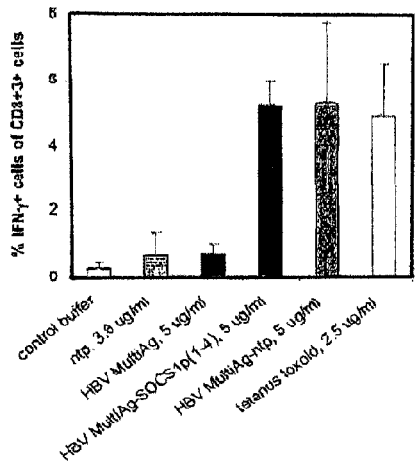
Fig 13a: CD8+ T cells
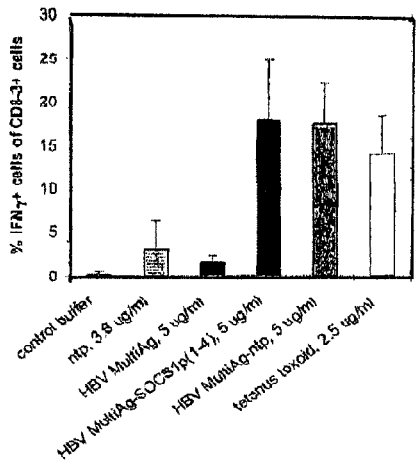
Fig 13b: CD4+ T cells
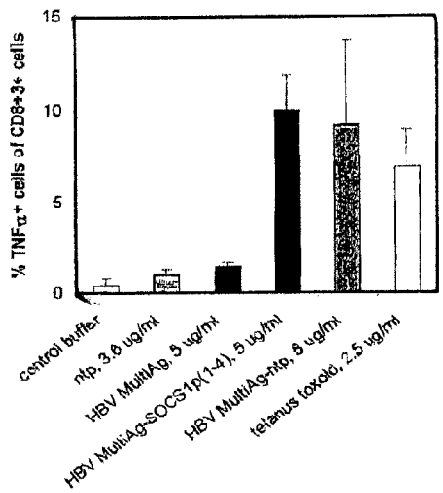
Fig 13c: CD8+ T cells
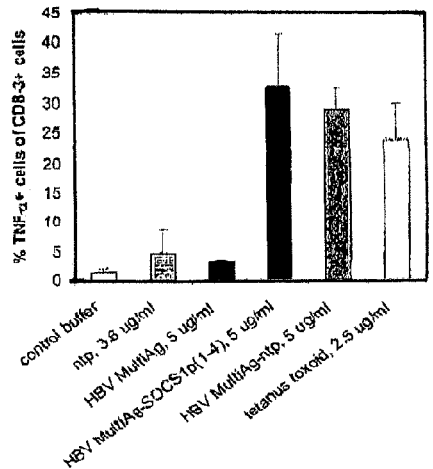
Fig 13d: CD4+ T cells

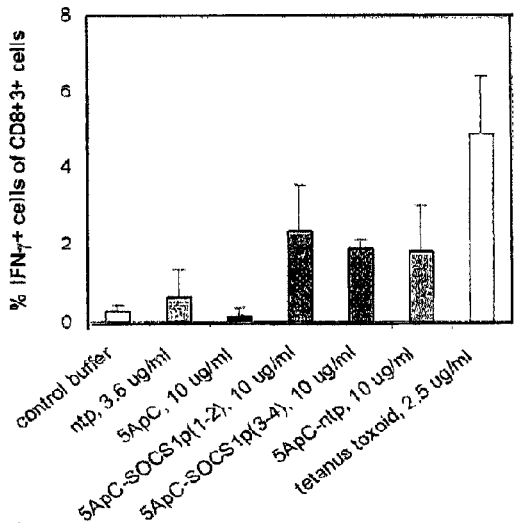
Fig 17a: CD8+ T cells
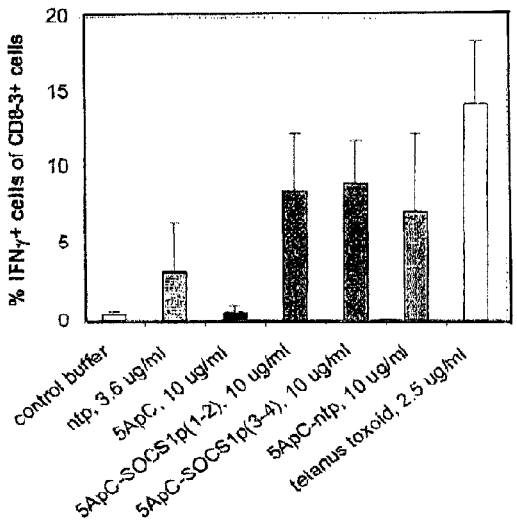
Fig 17b: CD4+ T cells
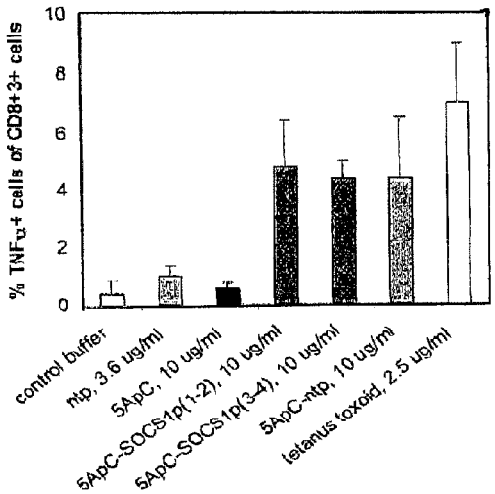
Fig 17c: CD8+ T cells
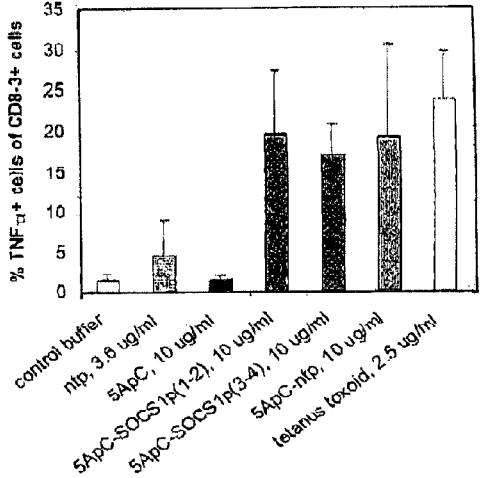
Fig 17d: CD4+ T cells

US 8,637,477 B2

ANTIGENIC COMPOSITIONS AND USE OF SAME IN THE TARGETED DELIVERY OF NUCLEIC ACIDS

FIELD OF THE INVENTION

The present invention relates to compositions for use in the delivery of nucleic acids. More particularly, chimeric antigens are provided for encapsulating, binding, or otherwise carrying and delivering nucleic acids to a target cell.

BACKGROUND OF THE INVENTION

Despite recent advances in the identification and refinement of nucleic acid therapeutics, finding suitable delivery means for these molecules in various applications has proved challenging. Moreover, while it is desirable to minimize the dosage of these expensive molecules, by localizing or targeting nucleic acid therapies to tissues/cells of interest, many technologies have been investigated, with few promising results.

RNAi [Fire A., et al (1998) Nature 391:801-11] has emerged as a means for sequence specific, posT transcriptional gene silencing, mediated by short interfering RNAs (siRNAs) homologous to the gene targeted for silencing. However, to be effectively used as drugs, the siRNAs (or their larger RNA precursors) must be delivered directly into the target cell. Targeted delivery of siRNA into specific cells of interest has been the main obstacle to achieving in vivo gene silencing by RNAi technologies. Specific delivery, dosage reduction, and minimizing toxicity are all important unmet objectives in this field.

Potential targeted siRNA delivery systems have emerged, such as antibody-mediated delivery, and liposomal delivery. Antibody mediated siRNA delivery may allow preferential accumulation of siRNA in target cells with less effect on normal tissues, and it has been suggested that such ligands can further be conjugated to delivery agents, such as liposomes, to promote uptake into target cells by receptor mediated endocytosis.

A further potential method for in vivo delivery of siRNA to specific target cells employs the nucleic acid binding properties of protamine, combined with the specificity of antibody-mediated delivery. Injection of siRNAs complexed with an antibody fragmenT protamine fusion protein have been used to selectively deliver siRNAs into target cells expressing the cell surface receptor recognized by the antibody [reviewed in Dykxhoorn, D. M., et al (2006) Gene Therapy 13-541-552; Song E. et al (2005) Nature Biotech. 23(6):709-717].

The specific cell type or targeted organ will generally vary with the type of therapeutic being delivered. For example, dendritic cells may be a key focus in cancer immunotherapy applications, as these potent antigen presenting cells are uniquely capable of inducing immunity to break tolerance to cancer antigens. It has been suggested that RNAi can be used for immune modulation by targeting gene expression in dendritic cells [Hill, J. A., et al (2003) J. Immunol. 171:691-696].

SOCS-1 has been shown to control the tolerogenic and immunogenic state of the dendritic cell, as well as the extent of antigen presentation and hence the magnitude of adaptive immunity [reviewed in Yoshimura, A., et al (2007) Nature Rev. Immunol. 7:454-465]. Silencing of SOCS-1 by siRNA enhances both antigen presentation by dendritic cells and antigen-specific anti-tumour immunity and may offer a selective means of breaking in host tolerance, of enhancing antigen-specific anti-tumour and anti-viral immunity, and of increasing the efficiency of dendritic cell-based cancer vaccines. Silencing SOCS-1 in dendritic cells may reduce the threshold of the cell's responsiveness to endogenous stimuli, permit persistent activation of antigen-specific T cells in vivo, and boost the anti-cancer activity of T cells.

In an ex vivo study, dendritic cells showed enhanced antigen-specific anti-tumour immunity when SOCS-1 was silenced in the dendritic cells before their vaccination with a cancer antigen [Shen, T. (2004) Nature Biotech 22(12): 1546-1553]. In an in vivo study in mice, silencing of SOCS-1 induced an anti-HIV-1 CD8+ and CD4+ T cell response as well as antibody responses [Song, X-T. et al (2006) PLoS Med 3:1-18].

The use of siRNA in the treatment of viral disease has also been suggested. In particular, the manifestation of chronic viral diseases relies on avoidance of the host immune system. It has been speculated that viral gene expression may be silenced by administration of virus-specific siRNA to the infected host.

In subjects with chronic viral or parasitic infections (where the organism is resident inside a host cell at some point during its life cycle), antigens are produced by and expressed in the host cell, and secreted antigens are present in the circulation. As an example, in the case of a chronic human hepatitis B virus (HBV) infected carrier, virions, HBV surface antigens, and a surrogate of the core antigens (in the form of the e-antigen) can be detected in the blood but are apparently tolerated by the host immune system.

Similarly, in cancer, tumour escape from immune surveillance and attack is a major determinant for tumour survival in the host. A need exists for new, therapeutically effective compounds, compositions and methods for eliciting or enhancing immune responses against infectious diseases or cancer, or to break tolerance to infectious diseases or cancer.

SUMMARY

In accordance with a first aspect of the invention, there is provided a method for inhibiting expression of a target gene within a target cell, the method comprising the steps of: providing a nucleic acid molecule suitable for effecting RNAi of a target gene; providing a chimeric antigen comprising: a nucleic acid binding domain comprising an amino acid sequence corresponding to HBV core protein or a fragment thereof, and a target binding domain comprising a ligand for binding to a receptor on a target cell; and administering the nucleic acid molecule and the chimeric antigen to the target cell.

In an embodiment, the step of administering the nucleic acid molecule and chimeric antigen to the target cell comprises mixing the nucleic acid molecule with a suitable amount of the chimeric antigen to create a nucleic acid delivery complex, and then administering the nucleic acid delivery complex to the target cell.

In various embodiments, the HBV Core protein fragment may be the assembly domain of HBV Core protein, the protamine domain of HBV Core protein, or any other suitable HBV Core protein fragment.

In certain embodiments, the nucleic acid binding domain may be operatively attached to the N-terminus or to the C-terminus of the target binding domain.

In an embodiment, the target cell is a mammalian host cell, and the step of administering the nucleic acid and chimeric antigen to the target cell comprises administering said nucleic acid and chimeric antigen to the mammalian host. in such embodiment, the target binding domain may comprise a xenotypic antibody fragment.

In accordance with a second aspect of the invention, there is provided a method for eliciting an immune response to a target antigen, the method comprising the steps of: providing a nucleic acid molecule suitable for effecting RNAi of a target gene; providing a chimeric antigen comprising: a nucleic acid binding domain comprising an amino acid sequence corresponding to HBV core protein or a fragment thereof, a target binding domain comprising a ligand for binding a receptor on an antigen presenting cell, and an immune response domain comprising a target antigen; and administering the nucleic acid molecule and the chimeric antigen to the target cell.

In an embodiment, the step of administering the nucleic acid molecule and chimeric antigen to the target cell comprises first mixing the nucleic acid molecule with a suitable amount of the chimeric antigen to create a nucleic acid delivery complex, and then administering the nucleic acid delivery complex to the target cell.

In various embodiments, the HBV Core protein fragment may be the assembly domain of HBV Core protein, the protamine domain of HBV Core protein, or any other suitable HBV Core protein fragment.

In certain embodiments, the nucleic acid binding domain may be operatively attached to the N-terminus or to the C-terminus of the target binding domain.

In an embodiment, the target binding domain comprises a xenotypic antibody fragment.

In specific embodiments, the target gene is an immunomodulatory gene or a viral gene, and the target antigen may be a cancer antigen, a viral antigen, or any other suitable antigen.

In accordance with another aspect of the invention, there is provided a composition for use in silencing the expression of a target gene within a target cell, the composition comprising: a nucleic acid sequence corresponding to the target gene; and a chimeric antigen comprising a nucleic acid interaction domain corresponding to HBV core protein or a fragment thereof, and a target binding domain operatively attached to the nucleic acid interaction domain, the target binding domain comprising a ligand for binding to a receptor on the surface of the target cell.

In certain embodiments, the target gene may be an immunomodulatory gene or a viral gene.

In an embodiment, the target binding domain is a xenotypic Fc fragment.

In various embodiments, the nucleic acid sequence is a siRNA, shRNA, antisense DNA, or plasmid for inhibiting expression of the target gene.

In suitable embodiments, the HBV core protein fragment may be the assembly domain, the protamine domain, or another fragment of HBV core protein.

In an embodiment, the binding of the ligand to receptor initiates internalization, for example by receptor-mediated endocytosis, of the chimeric antigen and nucleic acid.

In accordance with a further aspect of the invention, there is provided a chimeric antigen for use in delivering a nucleic acid to a target cell, the chimeric antigen comprising: a nucleic acid interaction domain corresponding to HBV core protein or a fragment thereof; and a target binding domain operatively attached to the nucleic acid interaction domain, the target binding domain comprising a ligand for binding to a receptor on the surface of the target cell.

In suitable embodiments, the HBV core protein fragment is the protamine domain of HBV core protein or the assembly domain of HBV Core protein.

In an embodiment, the nucleic acid interaction domain is attached to the C-terminus of the target binding domain.

In an embodiment, the chimeric antigen further comprises a second nucleic acid interaction domain operatively attached to the target binding domain, the second nucleic acid interaction domain corresponding to HBV core protein or a fragment thereof.

In further embodiments, the chimeric antigen further comprises an immune response domain comprising an antigenic amino acid sequence, operatively attached to the nucleic acid interaction domain, or to the target binding domain. The immune response domain may provide targeting to a secondary target cell.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 4b provides the nucleotide (SEQ ID NO:5) and amino acid sequence (SEQ ID NO:6) of the chimeric antigen depicted in FIG. 4a;

FIG. 7a-c are photographs of chimeric antigen particles;

FIG. 7d is a graph indicating the average size of the particles;

FIG. 13 a-d show production of IFN-γ and TNF-α in CD8+ and CD4+ T cells following stimulation with Chimigen® HBV S1/S2-Core Vaccine with encapsulated shRNA plasmid (SOCS1 or non-targeting);

FIG. 17 shows production of IFN-γ and TNF-α in CD8+ and CD4+ T cells after a second stimulation with chimeric antigen;

DETAILED DESCRIPTION

Generally, the present description, with reference to the Figures, provides chimeric antigen compositions for use in the delivery of nucleic acids to a target cell. The compositions include a Nucleic Acid Interaction Domain (NAID), and may be used to encapsulate, tether, or otherwise carry a nucleic acid. The compositions may be particularly useful in the delivery of immunotherapies, as delivery directly to antigen presenting cells, such as dendritic cells, is possible. Targeting to other cell types, for example hepatocytes, is also possible.

Chimigen® Vaccines

The Applicant has previously described chimeric antigens and methods for making same, for example in US 2004/0001853; US 2005/0013828; PCT/CA2004/001469; and US2005/0031628 to George et al, which are each incorporated herein by reference in their entirety. These prior patent applications describe chimeric antigens for use in targeting and activating antigen presenting cells (such as dendritic cells), inducing cellular and/or humoral immune responses, and in breaking host tolerance to chronic and/or viral infections. Also described are chimeric antigens in which an antigen of interest is combined with a xenotypic antibody fragment to improve immunogenicity, broadening the immune response. Chimeric antigens containing Hepatitis B virus (HBV) and Hepatitis C virus (HCV) proteins are also described.

Figure 1:
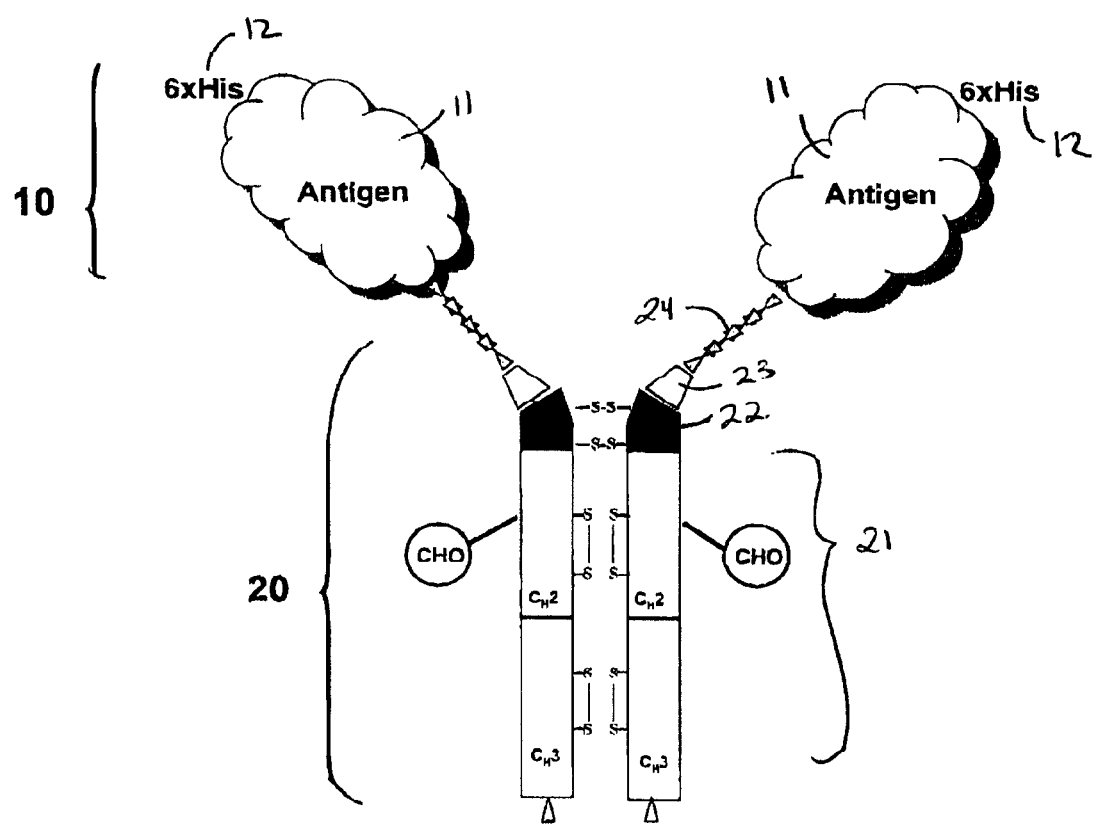
FIG. 1 is a schematic drawing of a chimeric antigen.

With reference to FIG. 1, the previously-described chimeric antigen structure (known as the Chimigen® molecule) shown has characteristics of both antigen and antibody, providing an adaptable platform capable of incorporating any desired antigen or combination of antigens. A xenotypic antibody fragment forms the target binding domain 20 for the antigen, enabling recognition of the Chimigen® Molecule as foreign, and thus more immunogenic. As a result, administration of the Chimigen® Molecule results in a broad immune reaction within the host. The antigen portion, or immune response domain 10, of the Chimigen® Molecule, provides an amino acid sequence against which a host immune response is desired. A cellular immune response (MHC class I) is therefore mounted to clear infected cells, cancer cells, or cells of interest that had been previously erroneously recognized as "self". A humoral immune response (MHC class II) is also mounted to enable the host to produce antibodies against the antigen of interest.

Moreover, when the Chimigen® Molecule is produced in insect cells, non-mammalian glycosylation is imparted to the molecule, which facilitates uptake of the Vaccine through host lectin receptors, and increases immunogenicity in the host. The structure of the basic Chimigen® Molecule is able to incorporate any antigen, and may be used to target multiple specific receptors on APC's or other cells of interest.

Various Chimigen® Vaccines have been described by the Applicant for prophylactic and/or therapeutic use, including vaccines directed to Hepatitis C, Hepatitis B, Western Equine Encephalitis, and Influenza.

With reference to US 20050013828, which is incorporated herein by reference, methods for incorporation of HBV proteins into the Chimigen® Vaccine structure are described. Specifically, HBV core protein was placed within the immune response portion 10 of the Chimigen® Molecule.

HBV Core Protein

Figure 2:
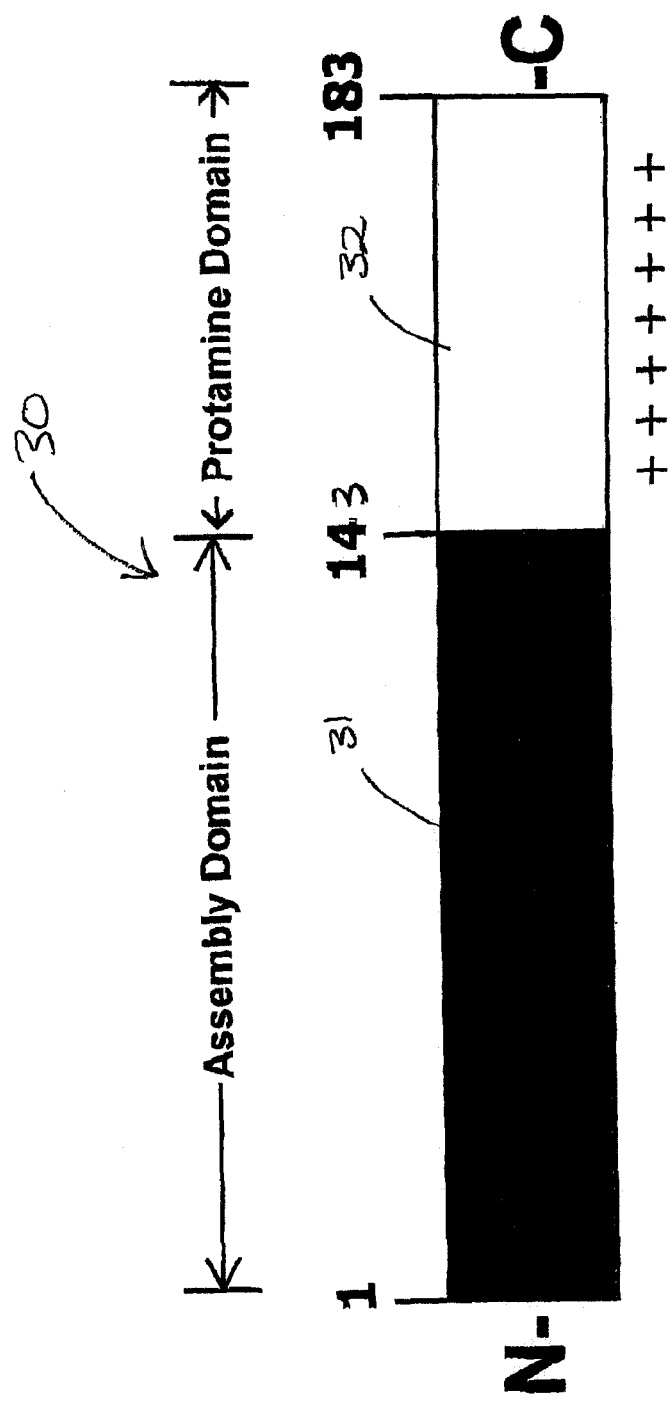
FIG. 2b provides the nucleotide (SEQ ID NO:1) and amino acid sequence (SEQ ID NO:2) of the HBV Core protein.

With reference to FIG. 2a, HBV Core protein 30 generally includes an assembly domain 31 (from N-terminus to approximately amino acid 143) and a protamine domain 32 (from approximately amino acid 144 to approximately amino acid 183). Nucleic acid and amino acid sequences of the HBV core protein 30 are provided in FIG. 2b. Notably, the assembly domain 31 allows aggregation of various core protein particles into a capsid form, while the protamine domain 32 is able to bind nucleic acids. While the aforementioned properties of these domains have been discussed generally in the prior art, it is shown here that these properties are retained even when corresponding peptides/portions are included within a larger molecule such as within the Chimigen® Molecule. Moreover, these properties may be exploited to produce a novel delivery system.

With reference again to FIG. 1, the Chimigen® Molecule includes an immune response domain 10, and a target binding domain 20. As will be described, the presently described chimeric antigens further comprise a nucleic acid interacting domain (NAID), which provides encapsulation of, binding to, or other means for attraction and retention of nucleic acids. The NAID may be inherent within or supplementary to the aforementioned immune response domain 10 and target binding domain 20. Specifically, the NAID may be provided by inclusion of HBV core protein or a fragment thereof within the Chimigen® Molecule. Thus, the presently described chimeric antigens may be used to carry therapeutic nucleic acids to a target cell.

Immune Response Domain

The immune response domain 10 of the chimeric antigen provides the desired antigenic properties. Typically, the immune response domain includes one or more antigens or antigenic fragments, or one or more recombinant antigens. Specifically, the immune response domain may include an antigen 11, which has been previously recognized as "self" by the host immune system. Further, the immune response domain may include a series of antigens to which immunity is desired.

The immune response domain may include, for example, an antigenic portion of an infectious agent, such as a virus or an obligate intracellular parasite, or of a cancer antigen. Examples of infectious viruses, obligate intracellular parasites and cancer antigens include those described in the published patent application PCT/CA2004/001469. The immune response domain of the chimeric antigen may further include a 6×His tag 12, fused to the one or more antigenic portions.

In certain embodiments, it may be desirable to include an antigen within the immune response domain that may provide some degree of binding to a target cell, to improve the specificity of delivery. For example, HBV S1/S2 binds to liver-derived HepG2 cells, and may be useful in targeting the chimeric antigen to hepatocytes.

Target Binding Domain

The target binding domain 20 binds to or otherwise directs the chimeric antigen to a target cell. Typically, the target binding domain is an antibody fragment capable of binding to a receptor on an antigen presenting cell, such as a dendritic cell, and which enables subsequent transport of the chimeric antigen into the antigen presenting cell by receptor mediated uptake. In addition, the glycosylation of the target binding domain facilitates the receptor-specific binding of the chimeric antigen to C-type lectin receptors on various cell types including antigen presenting cells.

The target binding domain 20 is formed from a xenotypic Fc fragment, which may extend from the C-terminal end to the immune response domain, and is typically recognized by the host as foreign, thereby increasing immunogenicity of the chimeric antigen. The target binding domain may provide customized delivery to a particular receptor on a specific cell type, for example FcγRI, FcγRII and FcγRIII (CD64, 32 and 16), on antigen presenting cells (such as dendritic cells) to bind, internalize, process, and present antigenic epitopes through MHC class I and MHC class II pathways to T and B cells and elicit a broad immune response. In this case, the epitopes ultimately presented by the antigen presenting cell may be epitopes from the immune response domain of the chimeric antigen.

When the chimeric antigen includes a NAID, the nucleic acid associated with the chimeric antigen may be similarly internalized within the antigen presenting cell. Further, the target binding domain may be designed as a ligand to provide selective binding with a specific receptor on a desired target cell type, leading to internalization of the chimeric antigen and associated nucleic acid within the target cell. For example, a target binding domain may be designed to bind Fcγ receptors on dendritic cells, or other antigen presenting cells, or designed to target lectin receptors.

In suitable embodiments, the target binding domain 20 includes a Fc fragment 21, a hinge region 22, and a portion of a $C_H1$ region 23. The chimeric antigen also includes a peptide linker 24 suitable for linking the target binding domain 20 to the immune response domain 10. The target binding domain may include an immunoglobulin heavy chain fragment, and may or may not include a hinge region. Details are provided in PCT/CA2004/001469, for example.

Testing to date has shown that Chimigen® Bionanoparticles bearing a xenotypic Fc domain and carrying siRNA directed to CD86 are able to deliver nucleic acid to dendritic cells and to effect RNAi as evidenced by down-regulation of CD86 in these cells (see examples below). Chimigen® Bionanoparticles were able to effect RNAi and immunomodulation in T cells.

Nucleic Acid Interacting Domain (NAID)

The Nucleic Acid Interacting Domain (NAID), is a portion of the presently described chimeric antigen that provides interaction with nucleic acids—encapsulating, sequestering, binding, or otherwise allowing the nucleic acid to be carried by the chimeric antigen to the target cell where it may be internalized upon meeting of the target binding domain with the target cell.

The NAID may be provided by incorporating a HBV core protein sequence within a chimeric antigen structure such as the Chimigen® Molecule. When a sequence corresponding to the assembly domain 31 of HBV core protein 30 is incorporated within the immune response domain 10 or within the target binding domain 20 of the chimeric antigen, the innate encapsulating ability of HBV core protein is retained within the chimeric antigen, enabling aggregation of chimeric antigen molecules. When the protamine domain 32 of the HBV core protein is incorporated within the chimeric antigen structure, the innate nucleic acid binding ability of the HBV core protein is retained within the chimeric antigen. When the entire HBV core protein 30 is present within the chimeric antigen, nucleic acid will be bound and a capsid will form about the nucleic acid. Each of the assembly domain 31 and the protamine domain 32 may be termed a NAID, as each interacts with nucleic acid for the purpose of delivery to a target cell. Specifically, the protamine domain 32 binds nucleic acid, while the assembly domain 31 encapsulates the bound nucleic acid.

Chimeric Antigens for Encapsulating Nucleic Acid

HBV core protein 30 or a fragment thereof may be incorporated within the immune response domain of the Chimigen® Molecule structure to enable aggregation about a nucleic acid. When a HBV core fragment is incorporated within the Chimigen® Molecule structure for this purpose, it is preferable that the fragment includes the assembly domain (amino acids 1-143 of SEQ ID NO:2, approx.) of HBV Core. The protamine domain (amino acids 144 to 183 of SEQ ID NO:2, approx.) may also be included. The HBV core sequence or fragment is preferably inserted into the Chimigen® Molecule at the C-terminus or within the immune response domain.

Additional antigens may be added to the N-terminus or C-terminus of the HBV core protein or fragment, or at a suitable location within the HBV core protein or fragment, for example at the immunodominant site between amino acid residues 79 (proline) and 80 (alanine) of HBV core.

Similarly, HBV core or a fragment thereof may be incorporated within the target binding domain of the Chimigen® Molecule, which also enables aggregation of the Chimigen® Molecule about nucleic acids. When a HBV core fragment attached in this manner, for example to the C-terminus of the Chimigen® Molecule, it is preferable that the fragment include at least the assembly domain (amino acids 1-143 of SEQ ID NO:2, approx.). The protamine domain (amino acids 144 to 183 of SEQ ID NO:2, approx.) may also be included.

Figure 5:
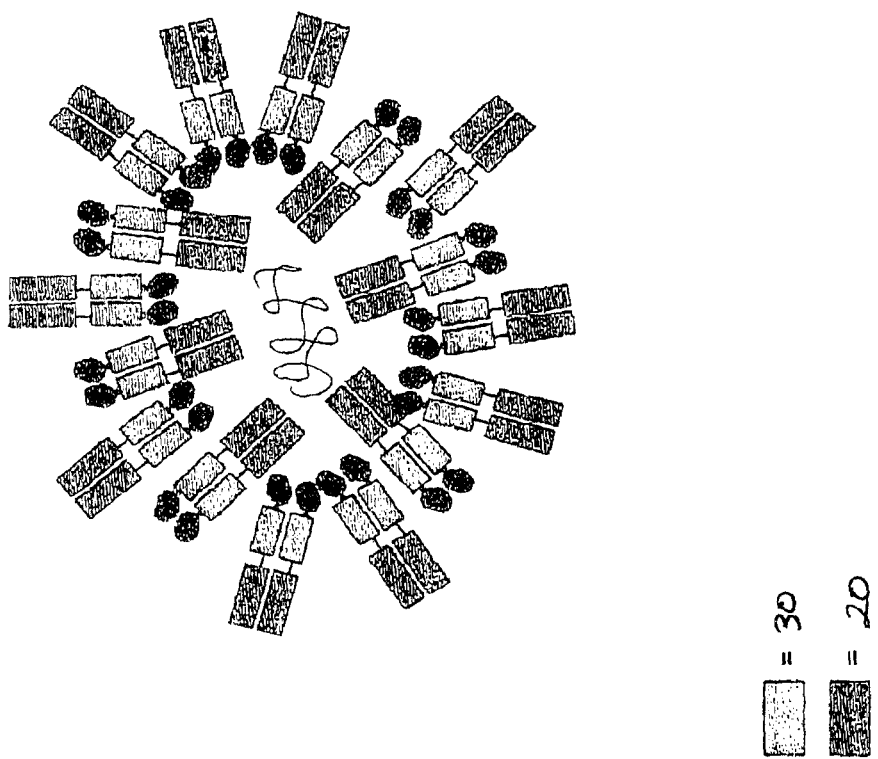
FIG. 5 is a schematic drawing of chimeric antigen aggregation about a nucleic acid molecule.
Figure 6:
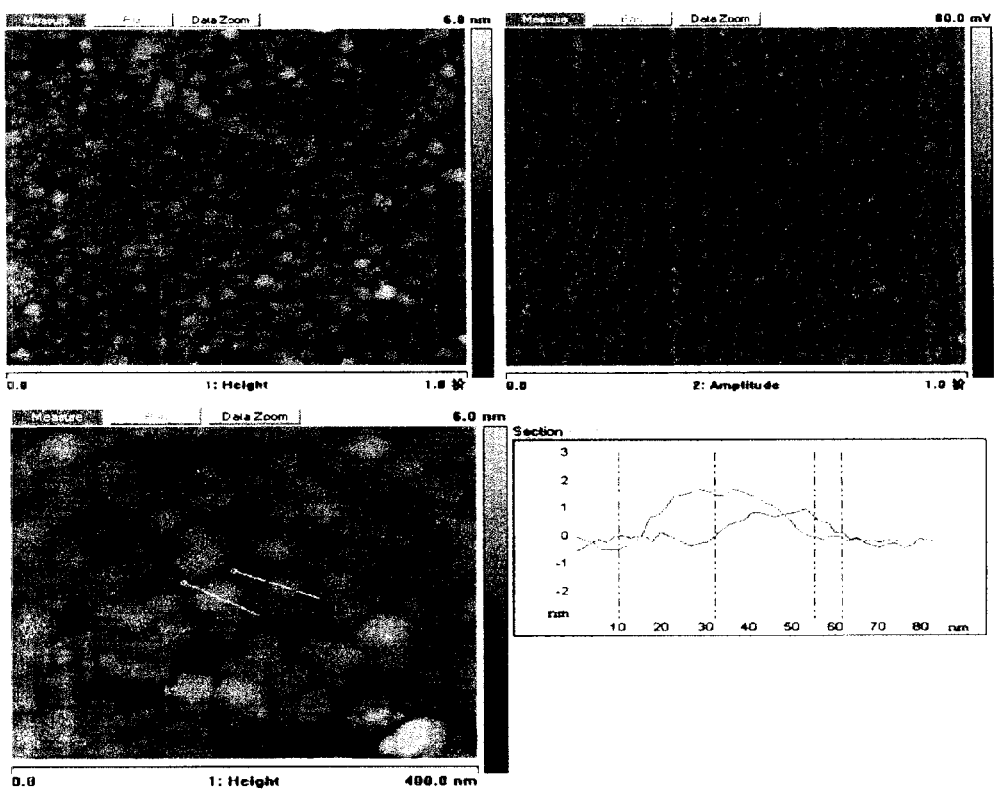
FIG. 6a-c are photographs of chimeric antigen particles.
FIG. 6d is a graph indicating the average size of the particles.

Aggregation of Chimigen® HBV Core Bionanoparticles about a nucleic acid is shown schematically in FIG. 5.

Chimeric Antigens for Binding Nucleic Acids

HBV Core Protein 30 or a protamine-like fragment 33 thereof may be incorporated within a chimeric antigen structure to enable direct binding to nucleic acid molecules. When a HBV core protamine-like fragment is incorporated within the Chimigen® Molecule for this purpose, it is preferable that the fragment include a significant portion of the protamine-like domain (eg. amino acids 144-184 of SEQ ID NO:2: ETTVVRRRDRGRSPRRRTP SPRRRRSQSPRRRRSQSR ES QC and provided as SEQ ID NO:7) of HBV Core. The HBV core or protamine-like fragment is preferably included within the immune response domain of the chimeric antigen or at the C-terminus.

Figure 3:
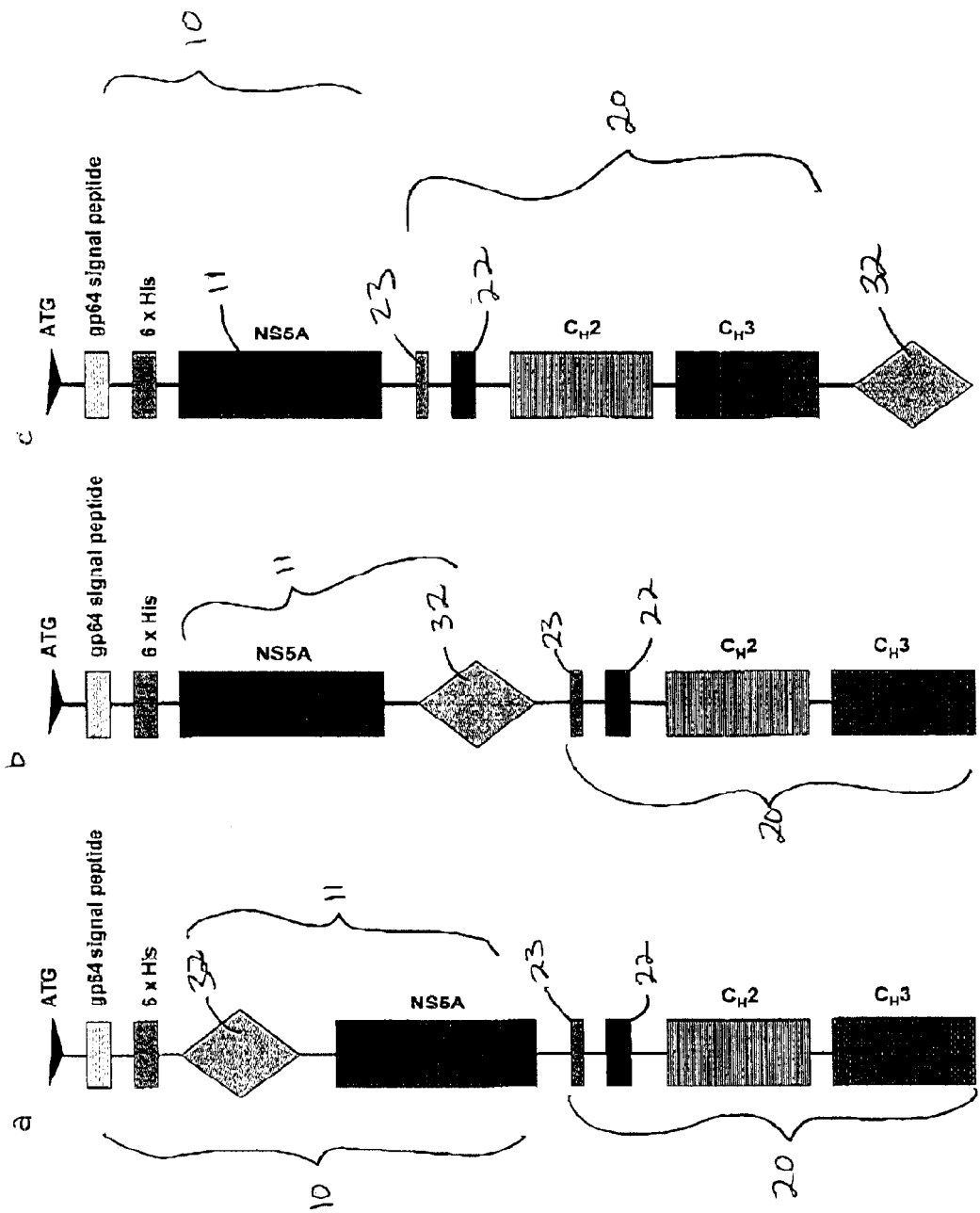
FIG. 3a-3c provide schematic drawings depicting three chimeric antigens in which the protamine domain of HBV Core provides a NAID.
FIG. 3d provides the nucleotide (SEQ ID NO:3) and amino acid sequence (SEQ ID NO:4) of the chimeric antigen depicted in FIG. 3c FIG. 4a provides a schematic drawing depicting a chimeric antigen in which the HBV Core protein sequence is included within the immune response domain to provide a NAID.

With reference to FIG. 3a-c, a schematic representation is shown of three fusion proteins, each incorporating HBV core protamine-like domain in various locations along the fusion protein, and with the HBV NS5A protein located in the immune response domain 10. With reference to FIG. 3c, the protamine-like fragment 33 extends from the C-terminus to the $C_H3$ domain. This Chimigen® Vaccine may be produced in plasmid pFastBacHTA-gp64 using the nucleic acid sequence shown in FIG. 3d. The resulting Chimigen® will bind nucleic acids at its C-terminal end and may be used to deliver nucleic acids to antigen presenting cells.

While this particular fusion protein was in fact able to bind nucleic acid, preliminary data indicates that this C-terminal protamine tail and nucleic acid binding location may impede interaction of the target cell receptors with the Fc portion of the chimeric antigen.

Introduction of Nucleic Acid to the Chimeric Antigen

The desired chimeric antigen may first be produced as a fusion protein, for example expressed in insect cells using the baculovirus expression system. The nucleic acid is synthesized separately, and mixed with chimeric antigen to form a chimeric antigen/nucleic acid complex.

When the chimeric antigen is intended to encapsulate nucleic acid, the purified fusion protein is produced, and nucleic acid is added under denaturing conditions. The denaturant is then removed by dialysis or gel filtration, and the chimeric antigen is renatured to form a Chimigen® Molecule/nucleic acid complex. The complex should be sufficiently stable so that, as the target binding domain binds to the receptors on the target cell, the nucleic acid, for example an siRNA, is delivered to the cytosol. The chimeric antigen is then processed through the antigen presentation pathways, while the siRNA interacts with RNA-induced silencing complex (RISC) in the cytosol, resulting in the annealing of the siRNA with the target mRNA and silencing the expression of the gene, via mRNA degradation.

When the chimeric antigen includes a C-terminal protamine tail, the nucleic acid may simply be prepared and added to the purified chimeric antigen.

Nucleic Acids

The Chimigen® Molecule is designed to bind to and be internalized by a target cell, carrying the associated (encapsulated or bound) nucleic acid molecule into the cytosol of the target cell. Accordingly, based on the nucleic acid to be delivered, an appropriate target cell type is selected, and the target binding domain is designed to bind a specific receptor on the target cell. For most applications, it is desirable to choose a target receptor that is specific to the target cell of interest, and to which an appropriate target binding domain may be specifically bound. Such care in design will minimize the amount of chimeric antigen and nucleic acid required, will improve potency, and also may minimize non-specific off-target effects. It should be noted that targeting of the chimeric antigen molecule to a particular cell type may also be accomplished by specific design of the immune response domain. For example, when HBV S1/S2 protein is used as an antigen within the immune response domain, targeting to hepatocytes is observed.

Nucleic acids for use with the presently described NAIDs include siRNA, dsRNA, shRNA, and plasmids, for example plasmids encoding shRNAs, which form a desirable siRNA sequence in situ. To date, plasmid DNA sequence of up to 5.3 kb have been encapsulated in Chimigen® Molecules.

U.S. Pat. No. 7,078,196 B2 and U.S. Pat. No. 7,056,704 B2 describe materials and methods for RNAi herein incorporated by reference. U.S. Pat. No. 7,056,704 B2, demonstrates, siRNA-mediated gene silencing in mammalian cells. U.S. Pat. No. 7,056,704 B2 also describes: a preferred structure of siRNA for efficient silencing; methods of preparing dsRNA for use in RNAi; and methods of mediating targeT specific nucleic acid modification, particularly RNAi and/or DNA methylation in a cell or an organism.

RNAi has been used for immune modulation by targeting gene expression in dendritic cells [Hill, J. A., et al (2003) *J. Immunol.* 171:691-696]. Silencing of SOCS-1 by siRNA was also shown to enhance both antigen presentation by dendritic cells and antigen-specific anti-tumour immunity. In an ex vivo study, dendritic cells showed enhanced antigen-specific anti-tumour immunity when SOCS-1 is silenced in the dendritic cells before their vaccination with a cancer antigen [Shen, T. (2004) *Nature Biotech* 22(12): 1546-1553]. In an in vivo study in mice, silencing of SOCS-1 induced an enhanced HIV-1 CD8+ and CD4+ T cell response as well as antibody responses [Song, X-T. et al (2006) *PLoS Med* 3:1-18].

Nucleic acid molecules for silencing SOCS-1 expression were delivered using the presently described Chimigen® Molecules, as described in the Examples section. Many other target genes would be suitable for delivery with the presently described chimeric antigens, as will be apparent to the reader upon reading of the present description combined with knowledge in the art.

Methods of Utilizing Chimeric Antigens and Nucleic Acids

As discussed above, chimeric antigens incorporating a Nucleic Acid Interaction Domain may be administered to a cell, tissue, target, or host along with nucleic acids. Such co-administered chimeric antigens and nucleic acids may be used to break host tolerance to an antigen, enhance immune responses, or to generate other desirable effects in antigen presenting cells or other cell types of interest. It is also contemplated that a chimeric antigen composition without a nucleic acid interaction domain may simply be co-administered with a nucleic acid(s). While this may provide some degree of efficacy, the co-administration of nucleic acid with chimeric antigen incorporating a NAID will provide a more specific and desirable effect, as both the chimeric antigen and nucleic acid are provided to the same cell or group of cells simultaneously.

The chimeric antigen (which may be a Chimigen® Molecule) will allow generation of a cellular and/or humoral immune response to the target antigen, which may have previously been recognized as "self" during a chronic infection, and which will then become recognized as "foreign." Accordingly, the host's immune system will mount a cytotoxic T lymphocyte response to eliminate the target antigen-infected cells. At the same time, antibodies produced by the host in response to the administered antigen will bind to the target antigen or infectious agent and remove it from the circulation or block binding of the target antigen or infectious agent to host cells. Accordingly, administration of a chimeric antigen along with an siRNA against a specific gene may induce a broad immune response in hosts who have chronic infections that are unrecognized or otherwise tolerated by the host immune system. Such administration may be used to break tolerance to a target antigen in a host who is chronically infected with an infectious agent, or who has a cancer or another immune disorder. For example, when the siRNA is designed to silence a viral gene product, such treatment may decrease viremia through RNAi, which may assist in clearing the infection. This will also be aided by the immune response generated by administration of the Chimigen® Vaccine.

While the Chimigen® Molecule is useful in eliciting or enhancing an immune response, the siRNA further silences a specific host gene. For example, the siRNA may further enhance the immune response to the Chimigen® Molecule by silencing the expression of a target gene, such as a gene encoding an inhibitor of cytokine signalling, for example silencing SOCS gene expression, and reducing SOCS-mediated inhibition of cytokine signaling.

The chimeric antigen and nucleic acid may be encapsulated together within a liposome. That is, the compositions of the present invention may be formulated for delivery either encapsulated in or attached to a lipid particle, a liposome, a vesicle, a nanosphere, or a nanoparticle or the like. Alternatively, compositions of the present invention can be bound, either covalently or non-covalently, to the surface of such carrier vehicles.

The Chimeric antigens and nucleic acids may be used for activating antigen presenting cells or enhancing antigen presentation in an antigen presenting cell (APC) in vivo or ex vivo. Antigen presenting cells contacted with the chimeric antigen and nucleic acid will result in binding and internalization of the chimeric antigen by APCs, activating the APCs and enhances antigen presentation of more than one epitope. This multi-epitopic response can include presentation of one or more epitopes of the immune response domain and/or presentation of one or more epitopes of the target binding domain.

An immune-treatable condition may be treated by co-administration, to a subject in need thereof, a therapeutically effective amount of a chimeric antigen and siRNA. Examples of immune-treatable conditions include viral infections such as HBV or HCV; parasitic infections; and cancers. For the treatment of HBV, suitable antigens for incorporation into the immune response domain of the Chimigen® Molecule may include at least one antigenic portion of a protein selected from the group consisting of a HBV Core protein, a HBV S protein, a HBV S1 protein, a HBV S2 protein, HBV Polymerase protein, HBV X protein, and/or combinations of same. For the treatment of HCV, the immune response domain may include at least one antigenic portion of a protein selected from the group consisting of HCV Core protein, E1 protein, E2 protein, NS2 protein, NS3 protein, NS4A protein, NS4B protein, NS5A protein, NS54B protein and/or combinations of same. HBV core protein or a fragment thereof may also be included within the immune response domain in order to provide encapsulation and/or binding of nucleic acid.

The amplitude of the immune response can be measured, for example, (i) by the amount of antigen-specific antibody present in the subject; (ii) by the amount of IFN-γ secreted by T cells in response to being exposed to APC loaded with the chimeric antigen or immune response domain alone; or (iii) by the amount of antigen-specific CD8+ T cells elicited in response to being exposed to APCs loaded with the chimeric antigen or immune response domain alone.

The chimeric antigen can be evaluated for its efficacy in generating an immune response by presenting the chimeric antigen to DCs ex vivo or in vivo. The DCs process and present the chimeric antigen to T cells, which are evaluated for proliferation of T cells and for the production of IFN-γ as markers of T cell response. Specifically, in the ex vivo situation, peripheral blood mononuclear cells (PBMCs) are isolated from naive donors, and are used for producing dendritic cells (DCs) and isolation of T cells. Activation of the T cells by the DCs is evaluated by measuring markers, e.g. IFN-γ levels, by a known procedure [See, e.g., Berlyn, et al., (2001) *Clin. Immunol.* 3:276-283]. A marked increase in the percentage of T cells induced to produce IFN-γ ex vivo will help predict efficacy in vivo. In the case of the in vivo situation, the chimeric antigen is directly introduced parenterally in the host where available DCs and other APCs have the capacity to interact with antigens and to process them accordingly.

The chimeric antigens and nucleic acids may also be used in prophylactically or therapeutically vaccinating a subject against an infection. The bifunctional nature of the molecule helps to target the antigen to APCs, e.g. DCs, making it a unique approach in the therapy of chronic infectious diseases by specifically targeting the APCs with the most effective stoichiometry of antigen to antibody. Such vaccines may be useful in the development of vaccines against infections caused by HBV, HCV, human immunodeficiency virus, human papilloma virus, herpes simplex virus, alphaviruses, influenza viruses, other types of viruses, obligate intracellular parasites and may also be applicable to all autologous antigens in diseases such as cancer and autoimmune disorders. The administration of these fusion proteins can elicit a broad immune response from the host, including both cellular and humoral responses. Thus, they can be used as therapeutic vaccines to treat subjects that are immune tolerant to an existing infection, in addition to being useful as prophylactic vaccines to immunize subjects at risk for developing a particular infection.

EXAMPLES

Example 1

Cloning and Expression of a Chimeric Antigen with a C-Terminal Protamine Tail Step 1. Cloning—

DNA encoding a target binding domain (TBD) containing a 5' Not I site and a 3' Xba I site was produced by PCR using previously generated pFastBacHTa-TBD as template with unique primers that add the respective restriction enzyme sites. The primers used were;

```
                                         (SEQ ID NO: 8)
5' Primer
5' TGTCATTCTGCGGCCGCAAGGCGGCGGGATCCGTGGACAAGAAAATT
GTGCCCAGG 3'

(SEQ ID NO: 9)
3' Primer
5' CCGGTCTAGATTCAGCCCAGGAGAGTGGGAGAG 3'.
```

The PCR fragment was isolated, digested with Not I and Xba I and cloned into a Not I/Xba I digested pFastBacHTa-gp64 plasmid.

For HBV Core protamine tail, the sequence was obtained by PCR of previously produced plasmid pFastBacHTa HBV Core-TBD as template using primers that add a unique Xba I site to the 5' end and a unique Hind III site to the 3' end. The primers used were:

```
                                         (SEQ ID NO: 10)
5' Primer:
5' CCGGTCTAGAGGAAACTACTGTTGTTAGACGAC 3'
and
                                         (SEQ ID NO: 11)
3' Primer:
5' GCGCAAGCTTTGACATTGAGATTCCCGAGATTG 3'
```

The PCR product was isolated, digested with Xba I/Hind III and cloned into a Xba I/Hind III sites of the re-cloned TBD plasmid, described above, to create pFastBacHTa-64 TBD-HBV Core protamine.

A chimeric antigen containing HCV NS5A as the antigen of the immune response domain was made by digesting the plasmid pFastBacHTa-gp64 TBD-HBV Core protamine with Xba I and Hind III and the TBD-HBV Core protamine tail fragment was isolated. The plasmid pFastBacHTa-gp64 HCV NS5A-TBD was digested with Xba I and Hind III and the TBD-HBV Core protamine tail fragment was cloned in.

Chimeric antigens encompassing the HBV Core protamine-tail domain located at various positions in the molecule were designed as follows (see FIG. 3 for schematic diagram). The HBV Core protamine tail domain DNA sequence was synthesized and subcloned into a generic pUC vector. The HBV Core domain was then digested with Bam HI/Eco RI or Not I restriction enzymes respectively and sub-cloned into the pFastBacHTa-gp64 NS5A TBD construct to generate two different clones: (1) pFastBacHTa-gp64-protamine NS5A TBD and (2) pFastBacHTa-64 NS5a-protamine TBD.

Step 2. Production of Recombinant Baculovirus for the Expression of Chimeric Antigen The expression of chimeric antigen NS5A-TBD-HBV Core protamine domain protein was performed using a baculovirus expression system in Sf9 insect cells. To generate recombinant baculoviruses encoding the chimeric antigen for expression, the Bac-To-Bac system (Invitrogen, Carlsbad, Calif., USA) was used. This system uses site-specific transposition with the bacterial transposon Tn7 to generate recombinant baculovirus in E. coli strain DH10Bac. The pFastBacHTa-gp64 HCV NS5A-TBD-HBV Core protamine plasmid has mini-Tn7 elements flanking the cloning site. The plasmid was used to transform E. coli strain DH10Bac, which has a baculovirus shuttle plasmid (bacmid) containing the attachment site of Tn7 within a LacZα gene. Transposition disrupted the LacZα gene so that only recombinant bacmids produced white colonies on plates containing X-gal/IPTG, and are easily selected for. The advantage of using transposition in E. coli is that single colonies contain only recombinant bacmids. The recombinant bacmid was isolated using standard plasmid isolation protocols and was used for the transfection of Sf9 insect cells to generate baculoviruses that express the chimeric antigen. The efficiency of the transfection was verified by checking for production of baculovirus DNA by PCR to screen for the inserted gene of interest. The expression of the heterologous protein in the transfected Sf9 cells was verified by SDS polyacrylamide gel electrophoresis (SDS-PAGE) and Western blots using the 6×His tag monoclonal antibody or anti mouse IgG1 (Fc specific) antibody as the probe. Once the production of recombinant baculovirus and the expression of chimeric protein were confirmed, recombinant virus was amplified to produce a concentrated stock of baculovirus.

Step 3. Production of Chimeric Antigen in Insect Cells

High titre recombinant baculovirus stocks were used to infect insect cells (eg. Sf9, High Five™). The infection is optimized, with respect to the MOI of the baculovirus, the period of the infection and the viability of the host cells. It is important to keep the viability of the insect cells at high levels to prevent degradation of the recombinant protein. The expressed proteins are purified by protocols developed for 6×His tagged proteins using affinity chromatography methods.

Figure 4A:
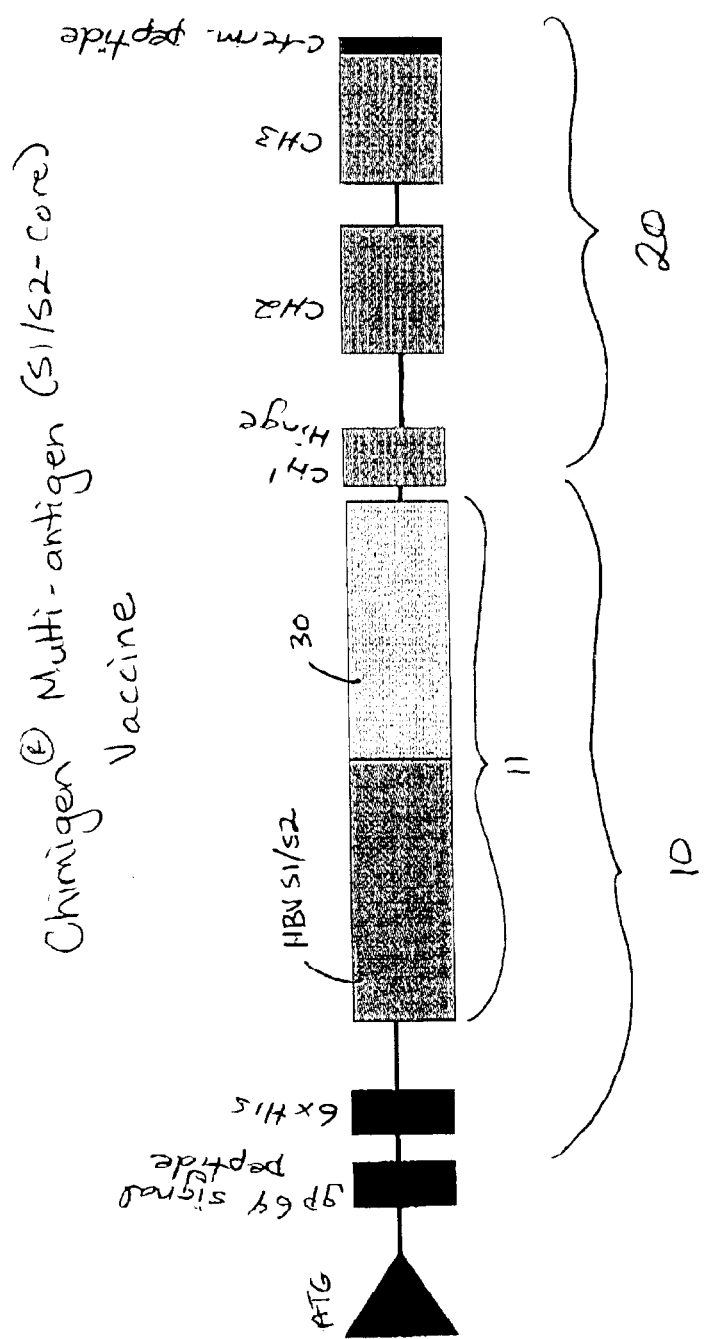

Some of the Chimigen® Molecules used in testing include:
Chimigen® HBV Core Vaccine—Chimigen® Molecule structure with HBV Core protein present in the immune response domain 10 as the antigen 11 and as a NAID.
Chimigen® HBV S1/S2 Core Vaccine—Chimigen® Molecule structure with HBV core protein and HBV S1/S2 protein in immune response domain. The structure of this Vaccine is shown in FIG. 4a, and the sequence is shown in FIG. 4b.
Chimigen® HBV Core Protamine Tail—Chimigen® Molecule structure with HBV Core protein present in the immune response domain 10 as the antigen 11 and a NAID, and with HBV Core protamine domain 32 also located at the C-terminus of the Chimigen® Molecule as a NAID.
Chimigen® HBV NS5A Protamine Vaccine—Chimigen® Molecule structure with HCV NS5A protein present in the immune response domain 10 as the antigen 11, and with HBV Core protamine domain 32 located at the C-terminus of the Chimigen® Molecule as a NAID.
Chimigen® HBV Protamine tail HCV NS5A vaccine—Chimigen® Molecule structure with both the protamine domain 32 of HBV Core and HCV NS5A in the immune response domain 10.

Example 2

Visualization of Chimigen Aggregation

Chimigen® HBV Core Vaccine and Chimigen® HBV S1/S2 Core Vaccine were visualized using Tapping Mode Atomic Force Microscopy (TM-AFM). The images generated are shown in FIG. 6a-d and 7a-d, respectively. As indicated, the aggregates/nanoparticles formed are of uniform size and ellipsoid shape, having a diameter of 30-40 nm and a height of 2 nm.

Example 3

Encapsulation of shRNA Plasmid by Chimigen® S1/S2 Core Vaccine

Figure 8A:
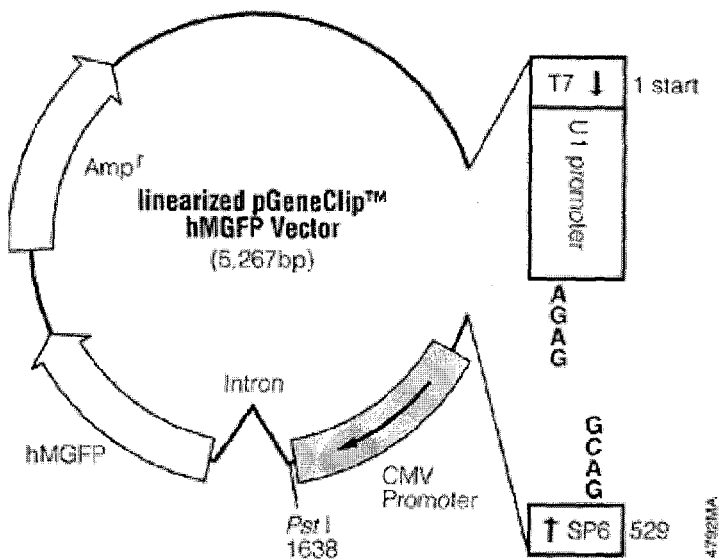
FIG. 8a shows the structure of the GFP vector plasmid used in testing.
Figure 8B:
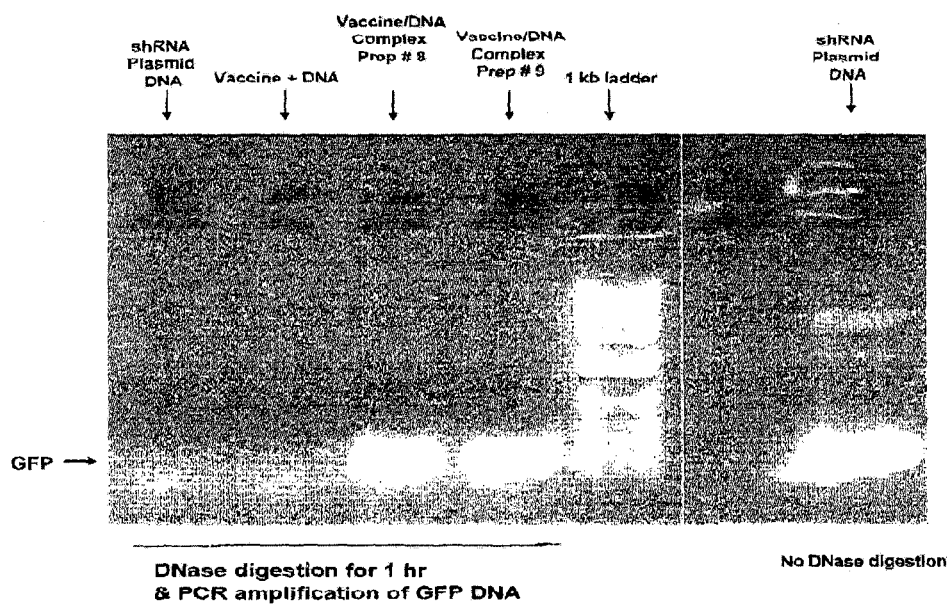
FIG. 8b is a photograph of DNase digestion results in which DNA is protected from degradation by formation of a complex with a chimeric antigen vaccine.

SureSilencing shRNA plasmid was mixed with Chimigen HBV S1/S2 Core Vaccine under denaturing conditions. After removal of the denaturing conditions, encapsulation was evaluated by DNase treatment and PCR amplification of GFP DNA. The shRNA vector plasmid and results are shown in FIGS. 8a and 8b, respectively. It is noted that both vaccines protected the GFP DNA from DNAse treatment, suggesting that the vaccines are capable of forming encapsulated delivery vehicles around nucleic acids.

Example 4

Binding to Immature Dendritic Cells

Figure 9:
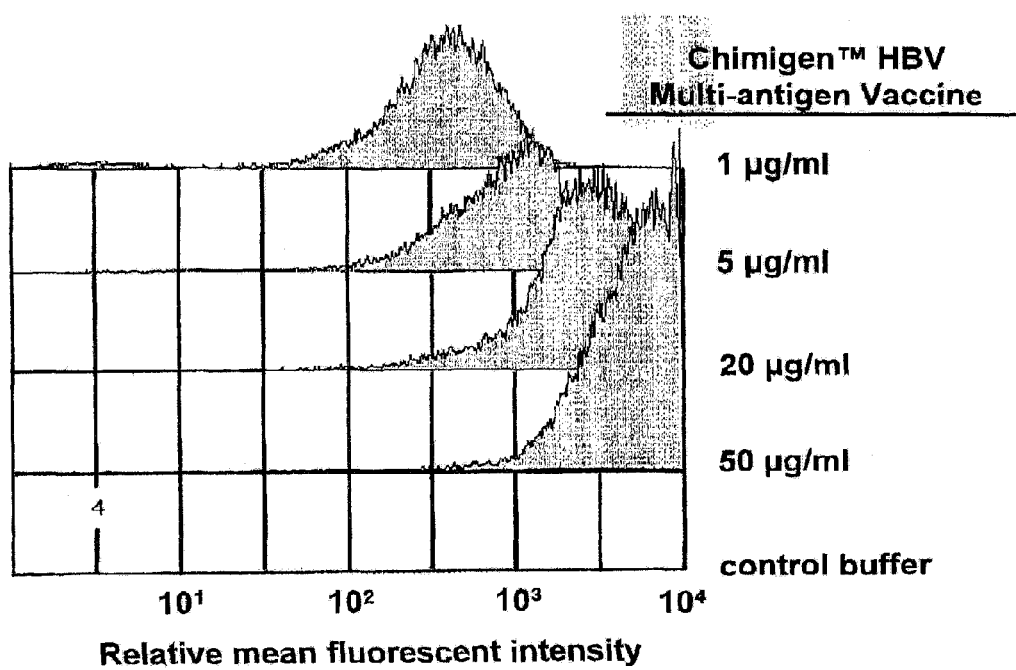
FIG. 9 shows binding of chimeric antigen vaccine to dendritic cells.

Binding of Chimigen® HBV S1/S2 Core Vaccine to immature DCs was investigated. Vaccine at 1-50 µg/ml was added for 1 hr at 4° C. to two day cultured PBMC-derived immature DCs. Bound vaccine was detected using anti-mouse IgG1-biotin and SA-PECy5 by flow cytometry. As shown in FIG. 9, vaccine bound at high levels to the immature DCs as indicated by the high relative mean fluorescence intensity (MFI) and was dose-dependent.

Example 5

Binding to HepG2 Cells

Figure 10:
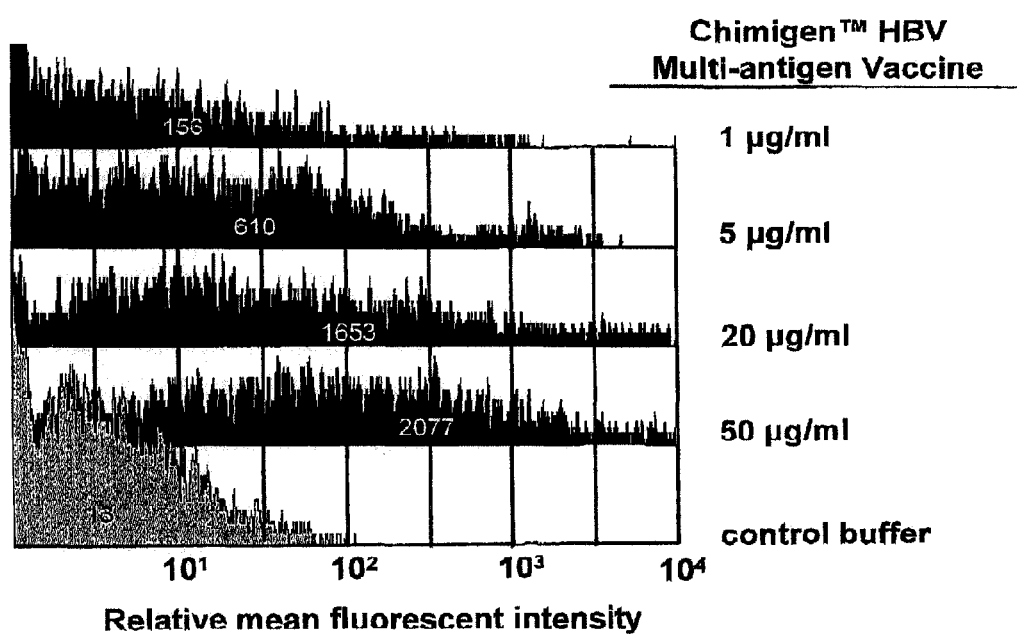
FIG. 10 shows binding of chimeric antigen vaccine to HepG2 cells.

Binding of Chimigen® HBV S1/S2 Core Vaccine to the liver cell line HepG2 was investigated. Vaccine at 1-50 µg/ml was added for 1 hr at 4° C. to HepG2 cells, and bound vaccine detected using anti-mouse IgG1-biotin and SA-PECy5 by flow cytometry. As shown in FIG. 10, the vaccine bound to HepG2 cells at a relatively high level in a dose-dependent manner.

Example 6

Combination of Vaccine with Nucleic Acid

Figure 11A:
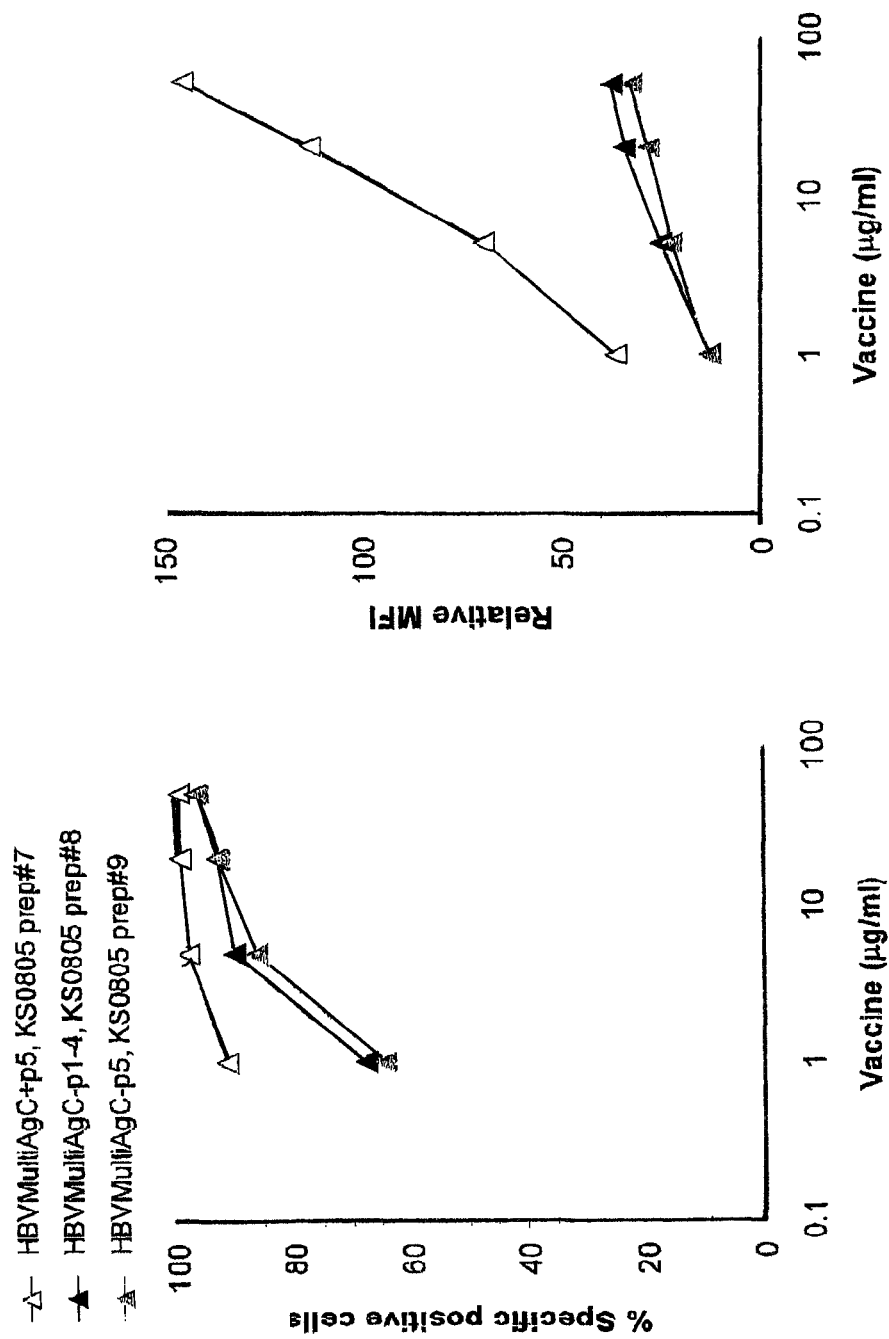
FIG. 11 shows binding of Chimigen® S1/S2 Core Vaccine with encapsulated shRNA to dendritic cells.
FIG. 11b shows binding of Chimigen® S1/S2 Core Vaccine with encapsulated siRNA to dendritic cells.

Binding of Chimigen® HBV S1/S2 Core Vaccine with encapsulated shRNA plasmid to immature DCs was investigated. Vaccine at 1-50 µg/ml with and without encapsulated shRNA plasmid was added for 1 hr at 4° C. to two day cultured PBMC-derived immature DCs. Vaccine binding was detected using anti-mouse IgG1-biotin and SA-PECy5 by flow cytometry. As shown in FIG. 11a, vaccine with encapsulated shRNA plasmid, either SOCS1 shRNA plasmids (plasmids 1-4) or non-targeting (control) shRNA plasmid (plasmid 5), bound to immature DCs. In comparison, vaccine without encapsulated shRNA plasmid (prep7) bound at higher levels than vaccine with encapsulated shRNA plasmid (prep8 and 9).

Chimigen® HBV S1/S2 Core Vaccine was combined with SOCS1 shRNA plasmids (Thermo Fisher Scientific) or with a control plasmid.

Chimigen® HBV S1/S2 Core Vaccine was combined with SOCS1 siRNA (commercially available). For non-targeting control siRNA, a pool of four double stranded RNAs was provided: GCAUCCGCGUGCACUUUCA (SEQ ID NO:12); GGUGGCAGCCGACAAUGCA (SEQ ID NO:13);

GGACGCCUGCGGAUUCUAC (SEQ ID NO:14); and UGUUAUUACUUGCCUGGAA (SEQ ID NO:15). For SOCS siRNA, a pool of four double stranded RNAs. The sense sequences were as follows: GACACGCACUUCCG-CACAUUU (SEQ ID NO:16); GCAUCCGCGUGCACU-UUCAUU (SEQ ID NO:17); GGUGGCAGCCGACAAUG-CAUU (SEQ ID NO:18); and GGACGCCUGCGGAUUCUACUU (SEQ ID NO:19).

Figure 11B:
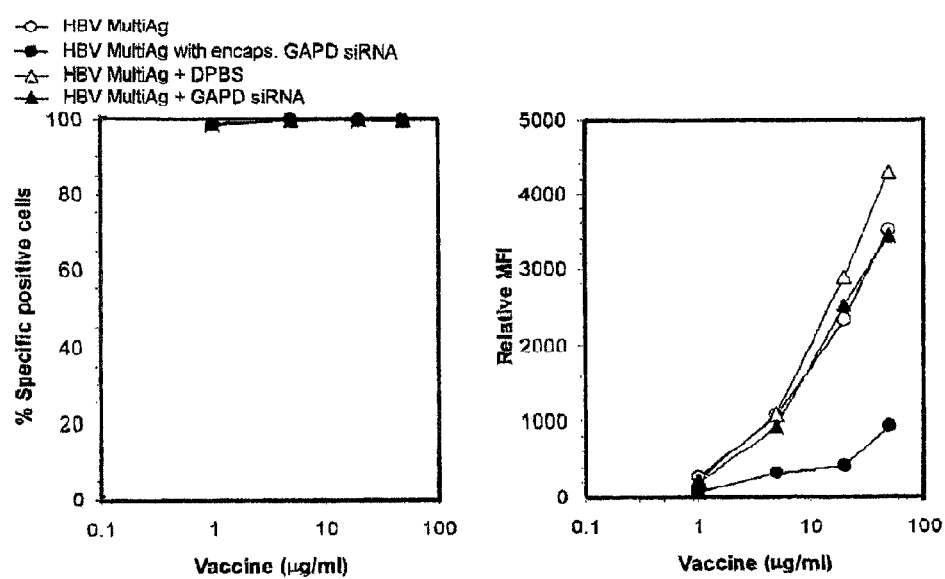

Binding of Chimigen® HBV S1/S2 Core Vaccine with encapsulated siRNA to immature DCs was investigated. Chimigen® HBV S1/S2 Core Vaccine (1-50 µg/ml) with and without encapsulated siRNA (GAPDH) was added for 1 hr at 4° C. to two day cultured PBMC-derived immature DCs. Vaccine binding was detected using anti-mouse IgG1-biotin and SA-PECy5 by flow cytometry. Vaccine was either encapsulated with GAPDH siRNA or was incubated with GAPDH for 60 min at room temperature (6:1 mole ratio of siRNA:vaccine). As shown in FIG. 11b, siRNA encapsulated with vaccine bound to immature DCs at a high level in a dose-dependent manner. In comparison, vaccine without encapsulated siRNA bound at higher levels than vaccine with encapsulated siRNA.

Chimigen® HCV NS5A-Protamine Tail Vaccine was combined with CD86 siRNA. The vaccine was incubated with CD86siRNA for 1 hour at room temperature at a 6:1 molar ratio.

Example 7

Antigen Presentation Assay

PBMC-derived monocytes were differentiated to immature dendritic cells, which were then loaded with vaccine; shRNA plasmid; or vaccine with shRNA plasmid (SOCS1 or non-targeting). T cells were isolated from autologous PBMC's and cultured with antigen-loaded dendritic cells. T cells were restimulated after 11 days of culture.

T cells were investigated for their functional response to DCs loaded with Chimigen® shRNA plasmid encapsulated Vaccine. PBMC-derived monocytes were differentiated to immature DCs which were then loaded with vaccine, shRNA plasmid, or Chimigen® HBV S1/S2-Core Vaccine encapsulated with shRNA plasmid (SOCS1 or non-targeting). T cells were isolated from autologous PBMCs and cultured with antigen-loaded DCs. Following 11 days of culture, T cells were re-stimulated with antigen-loaded DCs. For these experiments the DCs were not matured and exogenous IL-2 was not added to cell cultures.

Figure 12B:
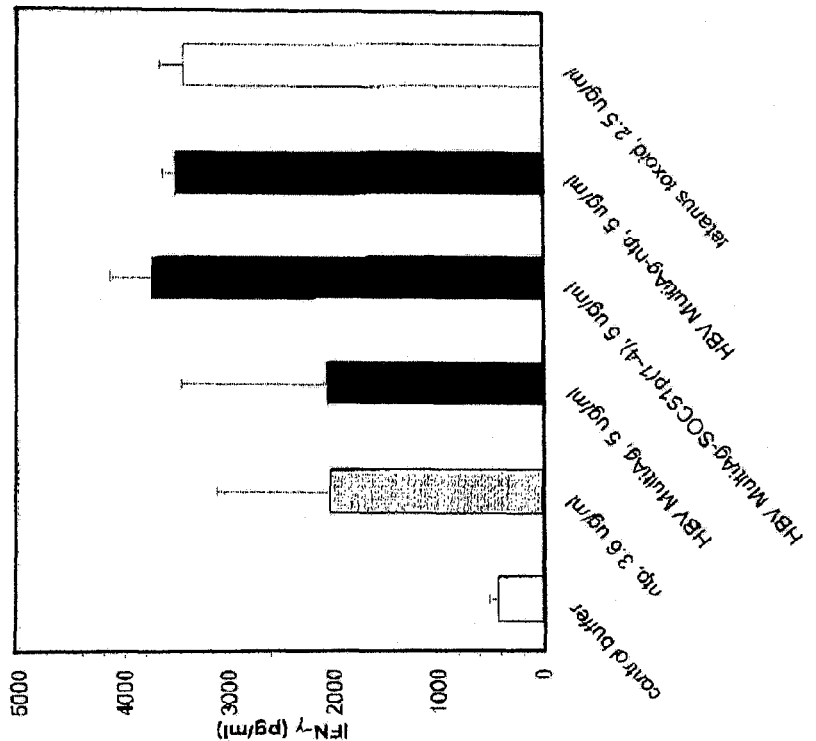
FIGS. 12 a and b show T cell production of IFN-γ after one and two stimulations with Chimigen® HBV S1/S2-Core Vaccine with encapsulated shRNA plasmid (SOCS1 or non-targeting)
Figure 12A:
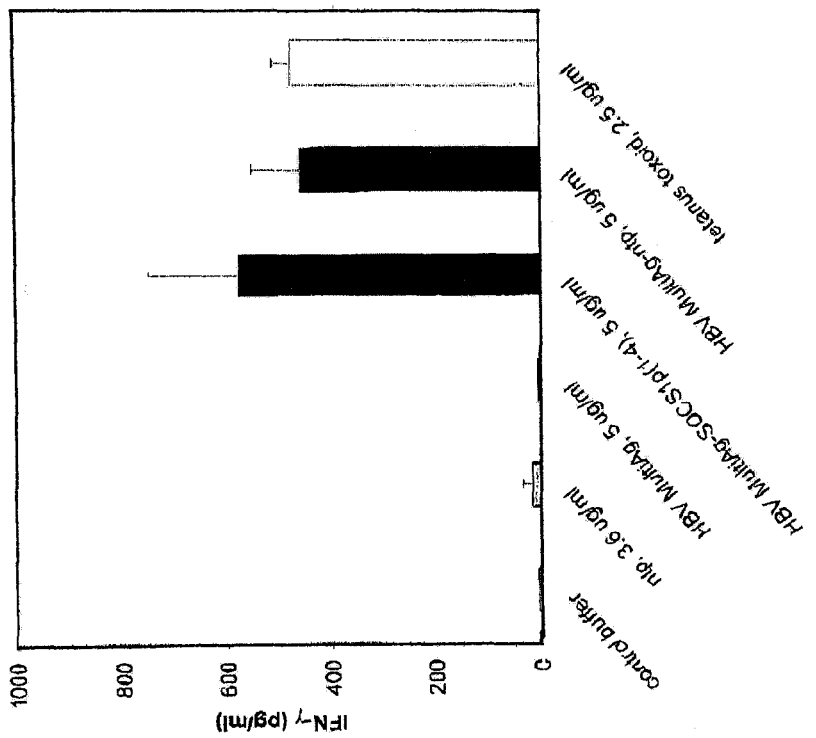

IFN-γ secretion was measured by ELISA after one and two stimulations. Results are shown in FIGS. 12a and 12b.

Following one and two stimulations, the production of IFN-γ in the T cell cultures was assessed by ELISA. As shown in FIGS. 12a and 12b, the cultures stimulated with Chimigen® HBV S1/S2-Core Vaccine encapsulated with shRNA plasmid (SOCS1 or non-targeting) produced a marked increased of IFN-γ compared with cultures stimulated with control buffer. Furthermore, cultures treated with encapsulated vaccine produced a greater amount of IFN-γ compared with cultures treated with non-encapsulated vaccine. These preliminary findings showed an increase in the amount of IFN-γ secretion in cultures stimulated with encapsulated SOCS1 shRNA plasmid versus non-targeting shRNA plasmid.

IFN-γ and TNF-α expression in CD8+ and CD4+ T cells was measures by intracellular cytokine labelling after two stimulations. Results are shown in FIG. 13a-d.

Six hours following a second stimulation, the production of IFN-γ and TNF-α in CD8+ and CD4+ T cells was assessed by intracellular cytokine labelling with detection by flow cytometry. As shown in FIG. 13a-d, the cultures stimulated with Chimigen® HBV S1/S2-Core Vaccine encapsulated with shRNA plasmid (SOCS1 or non-targeting) showed a marked increase in the percentage of IFN-γ+ and TNF-α+ CD8+ and CD4+ T cells compared to cultures stimulated with control buffer. Furthermore, cultures treated with encapsulated vaccine produced a greater amount of IFN-γ compared with cultures treated with non-encapsulated vaccine.

Example 8

Expansion of T Cells

Figure 14:
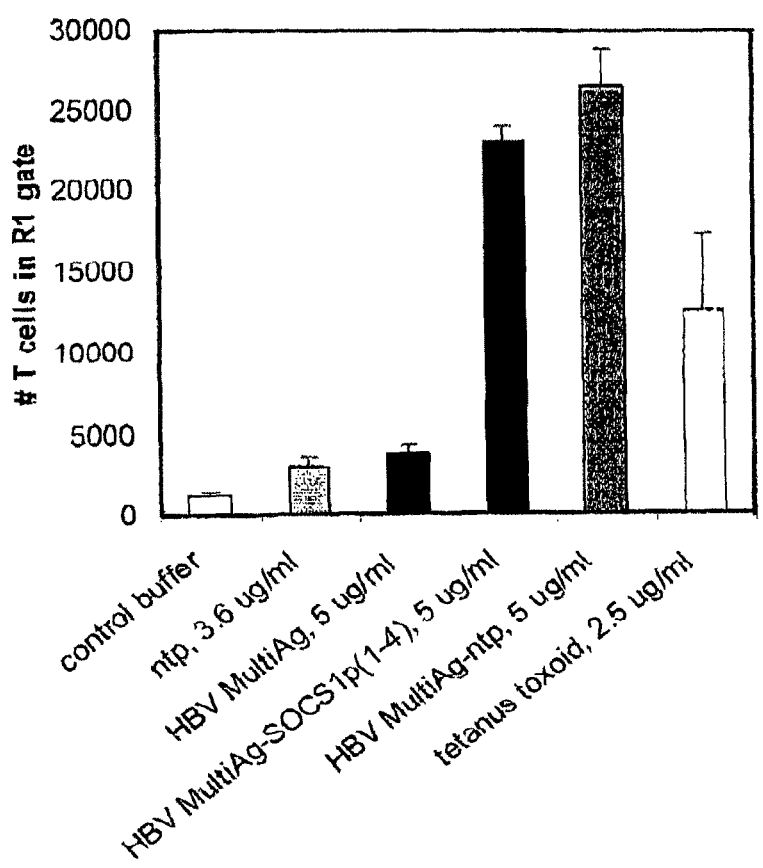
FIG. 14 shows expansion of T cells after chimeric antigen treatment.

An evaluation of the relative number of T cells in cultures treated with vaccine versus encapsulated vaccine is shown in FIG. 14. After 11 days of culture there was a significant expansion of T cells in culture upon stimulation with encapsulated vaccine versus non-encapsulated vaccine.

Example 9

Chimigen® HBV S1/S2 Core Vaccine

Figure 15:
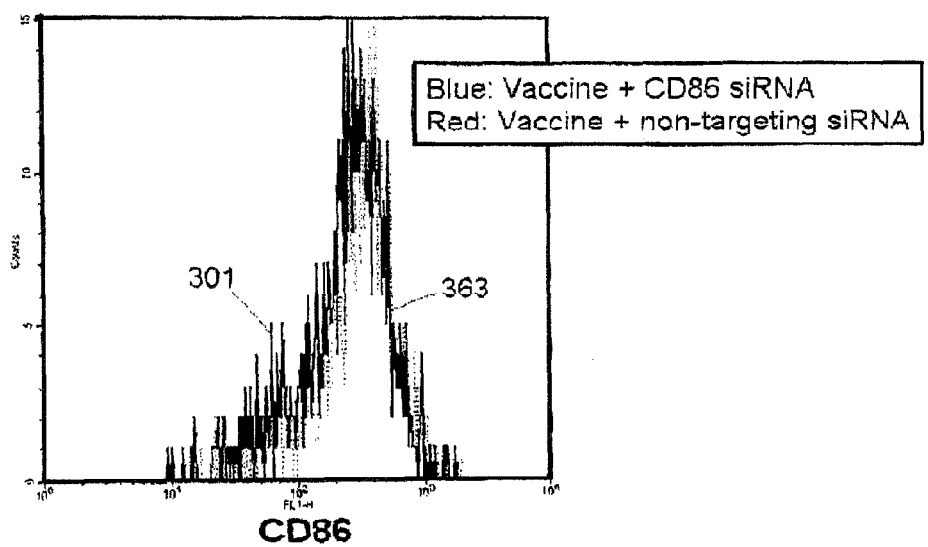
FIG. 15 shows CD86 expression in dendritic cells following chimeric antigen treatment.
Figure 16:
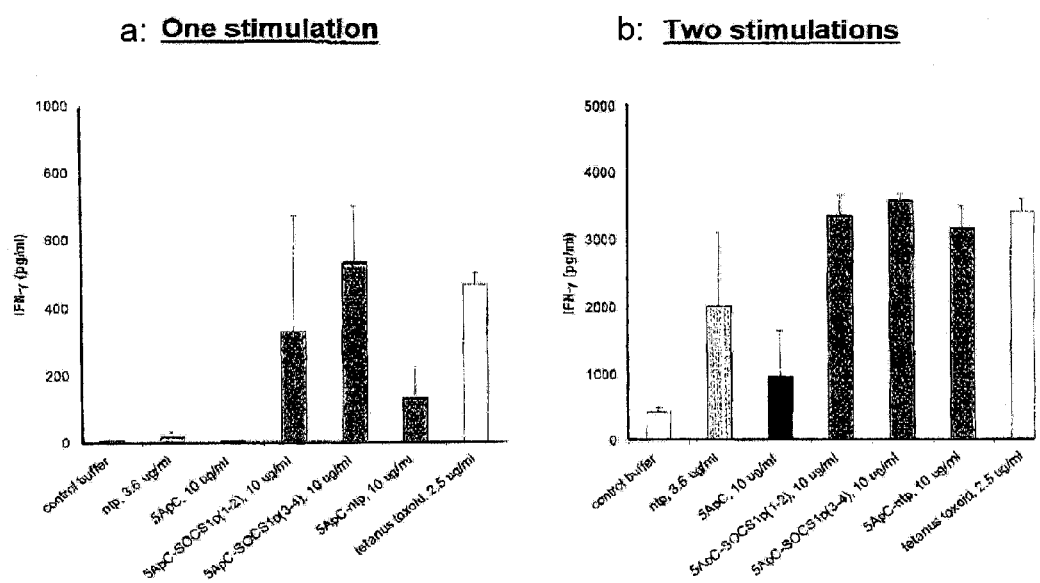
FIG. 16 shows production of IFN-γ in the T cell cultures following chimeric antigen treatment.

Immature dendritic cells were loaded with Chimigen® HBV S1/S2-Core Vaccine, CD86 siRNA, non-targeting siRNA, Chimigen® HBV S1/S2-Core Vaccine and CD86 siRNA, or Chimigen® HBV S1/S2-Core Vaccine and non-targeting siRNA. The DCs were then matured with LPS and assessed for CD86 expression by flow cytometry. Results are shown in FIG. 15. CD86 expression was down-regulated in DCs loaded with Chimigen® HBV S1/S2-Core Vaccine plus CD86 siRNA compared to Chimigen® HBV S1/S2-Core Vaccine plus non-targeting siRNA. These results suggest that Chimigen® HBV S1/S2-Core Vaccine plus CD86 siRNA resulted in the delivery of CD86 siRNA into the DC and resulted in a decrease in CD86 expression.

Example 10

Protamine Tail Vaccine Preparation

Chimigen® HBV Core Protamine Tail Vaccine was prepared by incorporation of the protamine-like domain of HBV core protein within the target binding domain. Specifically, the protamine-like domain was incorporated at the C-terminus of the target binding domain and the HBV NS5A antigen was incorporated within the immune response domain.

Example 11

Antigen Presentation Assay

T cells were investigated for their functional response to DCs loaded with Chimigen® NS5A Protamine Tail Vaccine with and without SOCS1 or non-targeting siRNA. PBMC-derived monocytes were differentiated to immature DCs which were then loaded with vaccine, siRNA, or Chimigen® HCV NS5A Protamine Tail Vaccine encapsulated with siRNA (SOCS1 or non-targeting). T cells were isolated from autologous PBMCs and cultured with antigen-loaded DCs. Following 11 days of culture, T cells were re-stimulated with antigen-loaded DCs. For these experiments the DCs were not matured and exogenous IL-2 was not added to cell cultures.

Following one and two stimulations, the production of IFN-γ in the T cell cultures was assessed by ELISA. As shown in FIGS. 16*a* and 16*b*, the cultures stimulated with Chimigen® HCV NS5A Protamine Tail Vaccine with siRNA (SOCS1 or non-targeting) produced a marked increased of IFN-γ compared with cultures stimulated with control buffer. Furthermore, cultures treated with vaccine and siRNA produced a greater amount of IFN-γ compared with cultures treated with vaccine alone. After a single stimulation, there was an increase in the amount of IFN-γ secretion in cultures stimulated with vaccine and SOCS1 siRNA versus non-targeting siRNA.

Six hours following a second stimulation, the production of IFN-γ and TNF-α in CD8+ and CD4+ T cells was assessed by intracellular cytokine labelling with detection by flow cytometry. As shown in FIG. 17*a-d*, the cultures stimulated with Chimigen® HCV NS5A Protamine Tail Vaccine with siRNA (SOCS1 or non-targeting) showed a marked increase in the percentage of IFN-γ+ and TNF-α+ CD8+ and CD4+ T cells compared with cultures stimulated with control buffer. Furthermore, cultures treated with vaccine and siRNA produced a greater amount of IFN-γ compared with cultures treated with vaccine only.

Example 12

Expansion of T Cells

Figure 18:
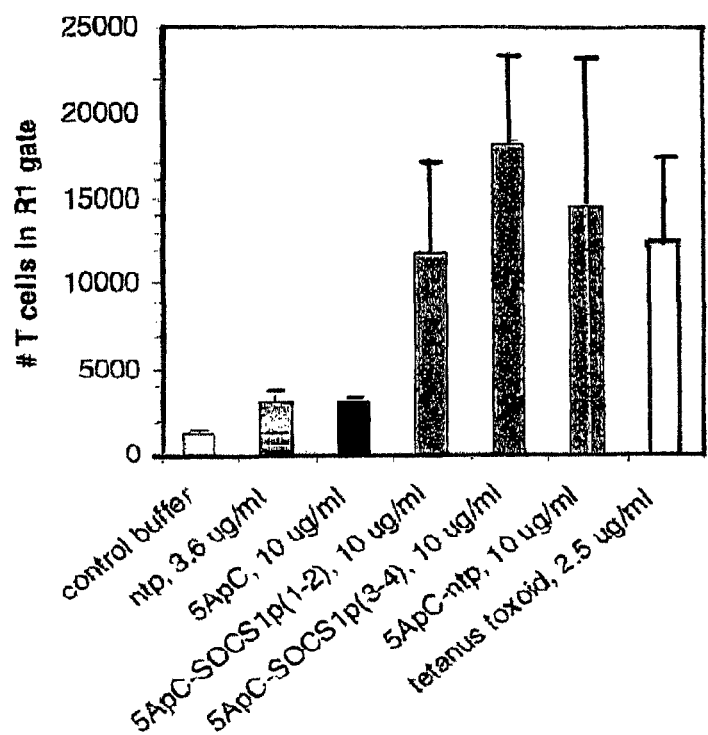
FIG. 18 shows T cell expansion after chimeric antigen treatment

An approximation of the relative number of T cells in cultures treated with vaccine versus vaccine and siRNA is shown in FIG. 18. After 11 days of culture there was a significant expansion of T cells in culture upon stimulation with vaccine and siRNA versus vaccine only. These preliminary findings showed that cultures stimulated with either vaccine and SOCS1 siRNA or with vaccine and non-targeting siRNA resulted in approximately equivalent numbers of T cells.

Example 13

RNAi of CD86 Expression

Figure 19:
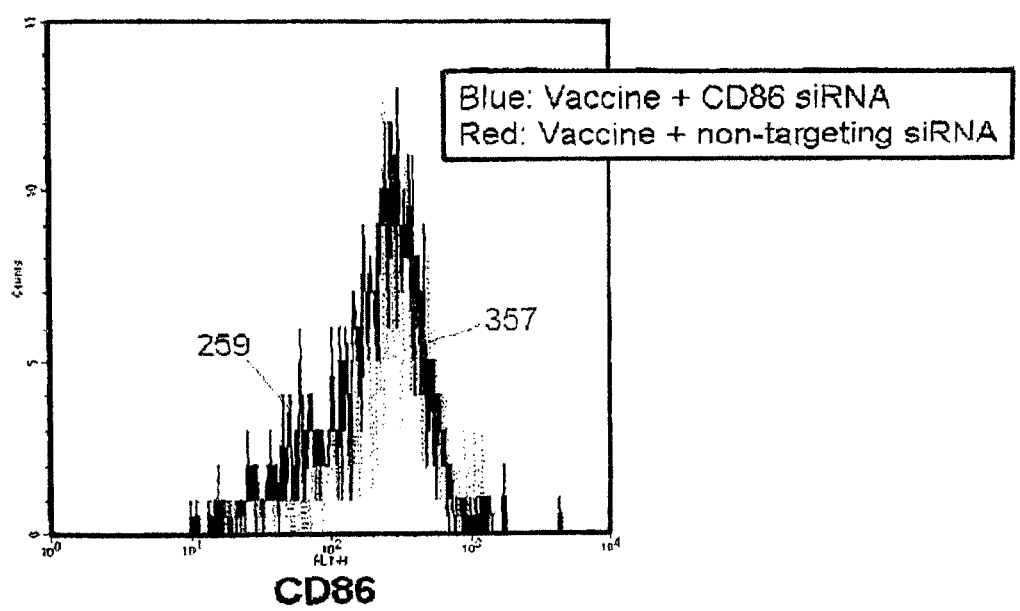
FIG. 19 shows CD86 expression after chimeric antigen treatment with or without CD86siRNA.

Immature dendritic cells were loaded with Chimigen® HCV NS5A Protamine Tail Vaccine, CD86 siRNA, non-targeting siRNA, Chimigen® NS5A Protamine Tail Vaccine and CD86 siRNA, or Chimigen® NS5A Protamine Tail Vaccine and non-targeting siRNA. The DCs were then matured with LPS and assessed for CD86 expression by flow cytometry. Results are shown in FIG. 19. These results suggest that Chimigen® NS5A Protamine Tail Vaccine plus CD86 siRNA resulted in the delivery of CD86 siRNA into the DC and the down-regulation of CD86 expression.

Example 14

Binding of Chimigen® HBV S1/S2 Core Vaccine to CD86 siRNA

Figure 20:
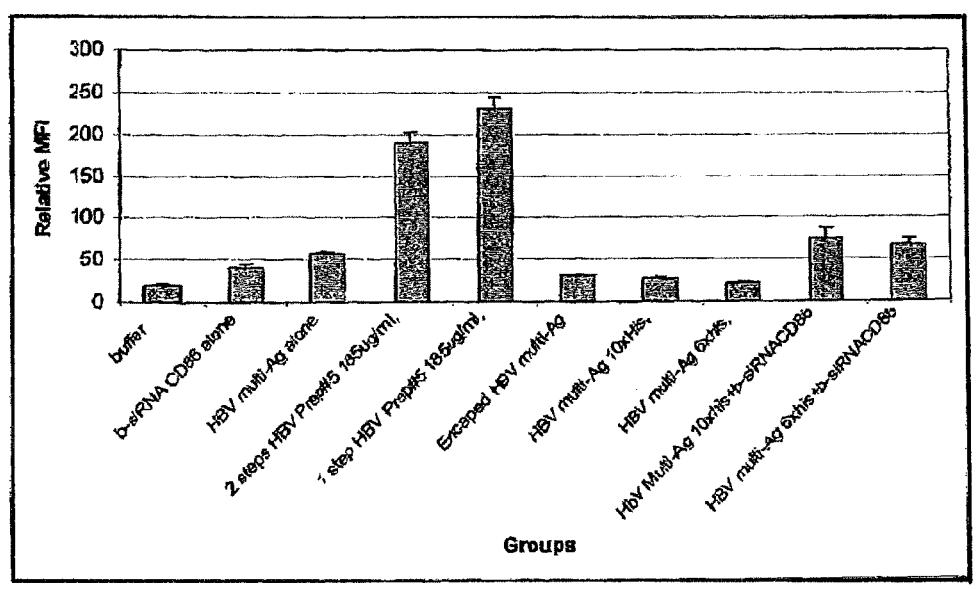
FIG. 20 shows binding of Chimigen® HBV S1/S2 Core Vaccine and siRNA complex to dendritic cells.

Binding of Chimigen® HBV S1/S2 Core Vaccine with biotin-labelled CD86 siRNA to immature DCs was investigated. Vaccine, vaccine and biotin-labelled CD86 siRNA, or CD86 siRNA was added for 1 hr at 4° C. to two day cultured PBMC-derived immature DCs. Binding was detected using SA-PECy5 by flow cytometry. As shown in FIG. 20, vaccine with biotin-labelled CD86 siRNA bound at relatively high levels to the immature DCs. Binding of biotinylated CD86 siRNA alone was not detected. These results indicate that siRNA binds Chimigen® HBV S1/S2 Core Vaccine, and that the vaccine and siRNA complex can bind to DCs.

Example 15

Internalization of Chimigen® HBV S1/S2 Core Vaccine and CD86 siRNA

Figure 21:
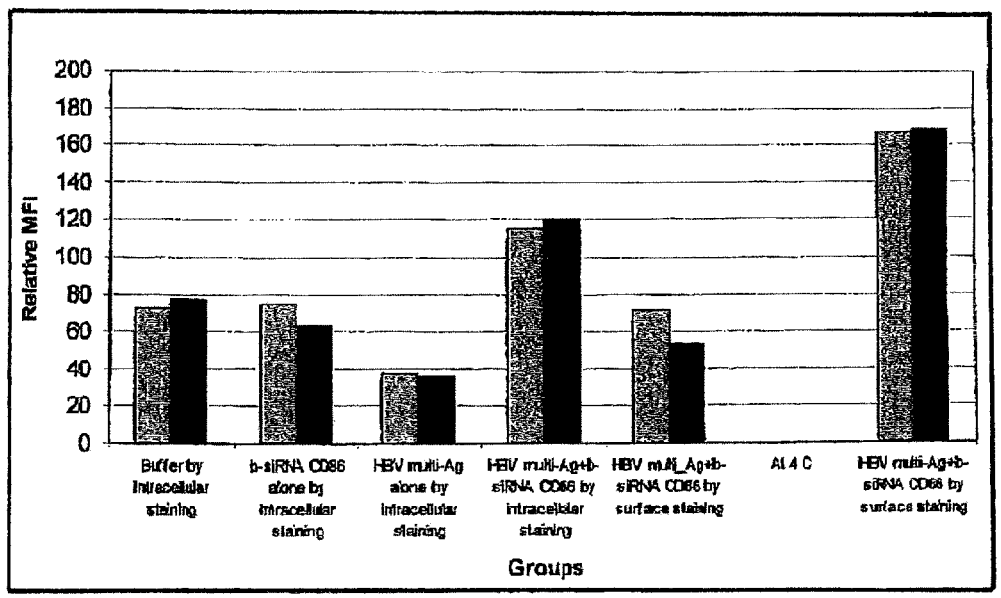
FIG. 21 shows dendritic cell fluorescence (internalization) after treatment with Chimigen® HBV S1/S2 Core Vaccine and CD86 siRNA complex.

Internalization of Chimigen® HBV S1/S2 Core Vaccine with biotin-labelled CD86 siRNA to immature DCs was investigated. Vaccine, vaccine and biotin-labelled CD86 siRNA, or CD86 siRNA was added for 1 hr at 4° C. and then 2 hr at 37° C. to PBMC-derived immature DCs (2 day cultured). Binding and internalization was detected by FACS after addition of SA-PECy5 with and without prior fixation and permeabilization. As shown in FIG. 21, fluorescence was detected in cells treated at 37° C. with vaccine and biotin-labelled CD86 siRNA but not with vaccine or biotinylated CD86 siRNA alone. As there was no fluorescence detected on the cell surface, it is concluded that the vaccine and siRNA was internalized. Thus siRNA and Chimigen® HBV S1/S2 Core Vaccine bind and are internalized by DCs.

Example 16

Protection of siRNA by Chimigen® HBV S1/S2 Vaccine

Figure 22:
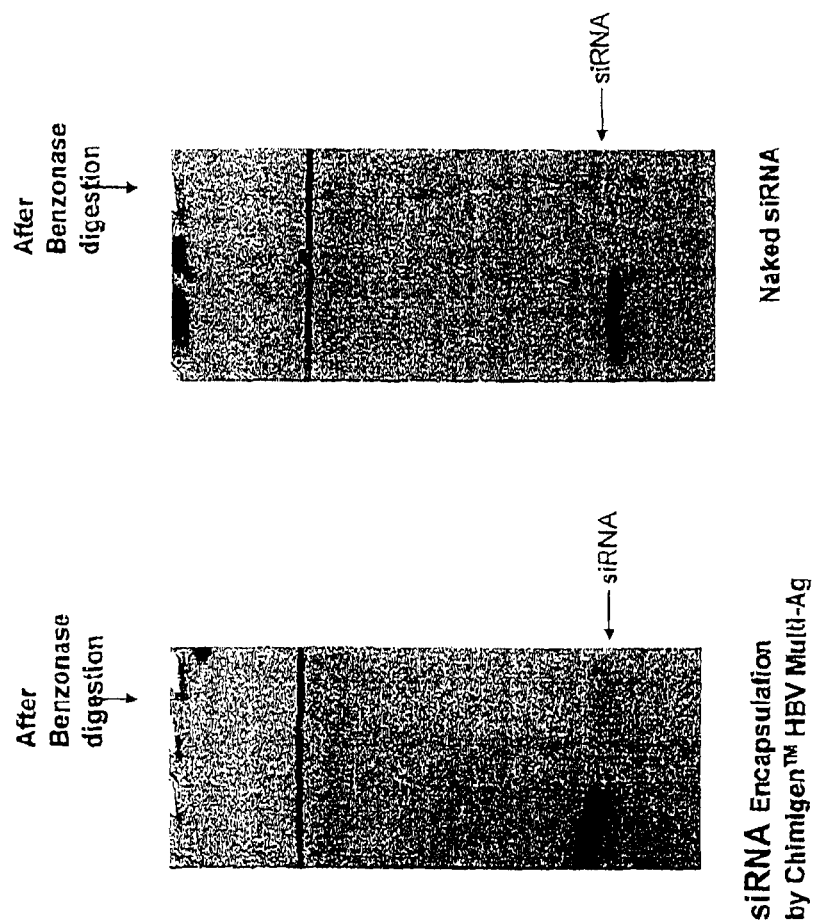
FIG. 22 shows the protection from benzonase treatment of siRNA by Chimigen® HBV S1/S2 Core Vaccine.

Encapsulated or naked siRNA was digested with Benzonase for 10 minutes at RT. The digested siRNA was separated on a SDS-PAGE gel containing 1 mM EDTA and was stained with 0.2% methylene blue. As shown in FIG. 22, the siRNA band is absent on the naked siRNA column, while present in the sample that was combined with Chimigen® HBV S1/S2 Vaccine (Multi-Ag).

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A method for inhibiting expression of a target gene within a target cell, the method comprising the steps of:
providing a nucleic acid molecule suitable for effecting RNAi of a target gene;
providing fusion protein comprising
a target binding domain for binding to a receptor on the surface of the target cell, the target binding domain comprising a hinge region, at least a portion of a $C_H1$ region and an Fc antibody fragment comprising a $C_H2$ and a $C_H3$ domain;
an immune response domain operatively attached to the target binding domain;
a first nucleic acid interaction domain corresponding to a HBV core protein or a fragment thereof operatively attached to the immune response domain; and
a second nucleic acid interaction domain operatively attached at the C-terminus of the target binding domain corresponding to the HBV core protein or a fragment thereof having at least the protamine domain of the HBV core protein; and
administering the nucleic acid molecule and the fusion protein to contact the target cell.

2. The method as in claim 1, wherein the nucleic acid molecule is mixed with a suitable amount of the fusion protein to create a nucleic acid delivery complex prior to contacting the target cell.

3. The method as in claim 1, wherein the HBV core protein fragment is the assembly domain of HBV core protein.

4. The method as in claim 1, wherein the nucleic acid binding domain is operatively attached to the C-terminus of the target binding domain.

5. The method as in claim 1, wherein the target cell is a mammalian host cell, and wherein the step of administering the nucleic acid and fusion protein to the target cell comprises administering said nucleic acid and fusion protein to the mammalian host.

6. The method as in claim 5, wherein the target binding domain comprises a xenotypic antibody fragment.

7. The method of claim 1, wherein the first nucleic acid binding domain comprises a fragment of the assembly domain of the HBV core protein and wherein the second nucleic acid binding domain comprises a fragment of the assembly domain and the protamine domain of the HBV core protein.

8. The method of claim 1, wherein the first nucleic acid binding domain comprises at least amino acids 1 to 78 of SEQ ID NO:2 of the HBV core protein and wherein the second nucleic acid binding domain comprises at least amino acids 81 to 183 of SEQ ID NO:2 of the HBV core protein.

9. The method of claim 1, wherein the immune response domain provides targeting to a secondary target cell.

* * * * *

SEQUENCE LISTING

<160> NUMBER OF SEQ ID NOS: 19

<210> SEQ ID NO 1
<211> LENGTH: 600
<212> TYPE: DNA
<213> ORGANISM: Hepatitis B virus
<220> FEATURE:
<221> NAME/KEY: CDS
<222> LOCATION: (1)..(600)

<400> SEQUENCE: 1

```
gac att gac cct tat aaa gaa ttt gga gct act gtg gag tta ctc tcg      48
Asp Ile Asp Pro Tyr Lys Glu Phe Gly Ala Thr Val Glu Leu Leu Ser
  1               5                  10                  15
```

```
ttt ttg cct tct gac ttc ttt cct tcc gtc aga gat ctc cta gac acc    96
Phe Leu Pro Ser Asp Phe Phe Pro Ser Val Arg Asp Leu Leu Asp Thr
         20                  25                  30 gcc tcg gct ctg tat cgg gaa gcc tta gag tct cct gag cat tgc tca   144
Ala Ser Ala Leu Tyr Arg Glu Ala Leu Glu Ser Pro Glu His Cys Ser
     35                  40                  45 cct cac cat acc gca ctc agg caa gcc att ctc tgc tgg ggg gaa ttg   192
Pro His His Thr Ala Leu Arg Gln Ala Ile Leu Cys Trp Gly Glu Leu
 50                  55                  60 atg act cta gct acc tgg gtg ggt aat aat ttg gaa gat cca gca tcc   240
Met Thr Leu Ala Thr Trp Val Gly Asn Asn Leu Glu Asp Pro Ala Ser
 65                  70                  75                  80 agg gat cta gta gtc aat tat gtt aat act aac atg gga tta aag atc   288
Arg Asp Leu Val Val Asn Tyr Val Asn Thr Asn Met Gly Leu Lys Ile
             85                  90                  95 agg caa ctc ttg tgg ttt cat atc tct tgc ctt act ttt gga aga gaa   336
Arg Gln Leu Leu Trp Phe His Ile Ser Cys Leu Thr Phe Gly Arg Glu
            100                 105                 110 act gta ctt gaa tat ttg gtc tct ttc gga gtg tgg att cgc act cct   384
Thr Val Leu Glu Tyr Leu Val Ser Phe Gly Val Trp Ile Arg Thr Pro
            115                 120                 125 cca gcc tat aga cca cca aat gcc cct atc tta tca aca ctt ccg gaa   432
Pro Ala Tyr Arg Pro Pro Asn Ala Pro Ile Leu Ser Thr Leu Pro Glu
130                 135                 140 act act gtt gtt aga cga cgg gac cga ggc agg tcc cct aga aga aga   480
Thr Thr Val Val Arg Arg Arg Asp Arg Gly Arg Ser Pro Arg Arg Arg
145                 150                 155                 160 act ccc tcg cct cgc aga cgc aga tct caa tcg ccg cgt cgc aga aga   528
Thr Pro Ser Pro Arg Arg Arg Arg Ser Gln Ser Pro Arg Arg Arg Arg
                165                 170                 175 tct caa tct cgg gaa tct caa tgt tcg cgg ccg ctt tcg aat cta gag   576
Ser Gln Ser Arg Glu Ser Gln Cys Ser Arg Pro Leu Ser Asn Leu Glu
                180                 185                 190 cct gca gtc tcg agg cat gcg gta                                    600
Pro Ala Val Ser Arg His Ala Val
                195                 200

<210> SEQ ID NO 2
<211> LENGTH: 200
<212> TYPE: PRT
<213> ORGANISM: Hepatitis B virus

<400> SEQUENCE: 2

Asp Ile Asp Pro Tyr Lys Glu Phe Gly Ala Thr Val Glu Leu Leu Ser
1               5                   10                  15

Phe Leu Pro Ser Asp Phe Phe Pro Ser Val Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125
```

-continued

```
Pro Ala Tyr Arg Pro Pro Asn Ala Pro Ile Leu Ser Thr Leu Pro Glu
        130                 135                 140

Thr Thr Val Val Arg Arg Asp Arg Gly Arg Ser Pro Arg Arg Arg
145                 150                 155                 160

Thr Pro Ser Pro Arg Arg Arg Ser Gln Ser Pro Arg Arg Arg
                165                 170                 175

Ser Gln Ser Arg Glu Ser Gln Cys Ser Arg Pro Leu Ser Asn Leu Glu
                180                 185                 190

Pro Ala Val Ser Arg His Ala Val
            195                 200

<210> SEQ ID NO 3
<211> LENGTH: 2406
<212> TYPE: DNA
<213> ORGANISM: Hepatitis B virus
<220> FEATURE:
<221> NAME/KEY: CDS
<222> LOCATION: (1)..(2406)

<400> SEQUENCE: 3 atg gta agc gct att gtt tta tat gtg ctt ttg gcg gcg gcg gcg cat      48
Met Val Ser Ala Ile Val Leu Tyr Val Leu Leu Ala Ala Ala Ala His
1               5                   10                  15 tct gcc ttt gcg tat ctg cag gta cgg tcc gaa acc atg tcg tac tac      96
Ser Ala Phe Ala Tyr Leu Gln Val Arg Ser Glu Thr Met Ser Tyr Tyr
            20                  25                  30 cat cac cat cac cat cac gat tac gat atc cca acg acc gaa aac ctg     144
His His His His His His Asp Tyr Asp Ile Pro Thr Thr Glu Asn Leu
        35                  40                  45 tat ttt cag ggc gcc atg gat ccg gaa ttc tcc ggt tcc tgg cta agg     192
Tyr Phe Gln Gly Ala Met Asp Pro Glu Phe Ser Gly Ser Trp Leu Arg
50                  55                  60 gac atc tgg gac tgg ata tgc gag gtg ctg agc gac ttt aag acc tgg     240
Asp Ile Trp Asp Trp Ile Cys Glu Val Leu Ser Asp Phe Lys Thr Trp
65                  70                  75                  80 ctg aaa gcc aag ctc atg cca caa ctg cct ggg att ccc ttt gtg tcc     288
Leu Lys Ala Lys Leu Met Pro Gln Leu Pro Gly Ile Pro Phe Val Ser
                85                  90                  95 tgc cag cgc ggg tat agg ggg gtc tgg cga gga gac ggc att atg cac     336
Cys Gln Arg Gly Tyr Arg Gly Val Trp Arg Gly Asp Gly Ile Met His
            100                 105                 110 act cgc tgc cac tgt gga gct gag atc act gga cat gtc aaa aac ggg     384
Thr Arg Cys His Cys Gly Ala Glu Ile Thr Gly His Val Lys Asn Gly
        115                 120                 125 acg atg agg atc gtc ggt cct agg acc tgc agg aac atg tgg agt ggg     432
Thr Met Arg Ile Val Gly Pro Arg Thr Cys Arg Asn Met Trp Ser Gly
130                 135                 140 acg ttc ccc att aac gcc tac acc acg ggc ccc tgt act ccc ctt cct     480
Thr Phe Pro Ile Asn Ala Tyr Thr Thr Gly Pro Cys Thr Pro Leu Pro
145                 150                 155                 160 gcg ccg aac tat aag ttc gcg ctg tgg agg gtg tct gca gag gaa tac     528
Ala Pro Asn Tyr Lys Phe Ala Leu Trp Arg Val Ser Ala Glu Glu Tyr
                165                 170                 175 gtg gag ata agg cgg gtg ggg gac ttc cac tac gta tcg ggt atg act     576
Val Glu Ile Arg Arg Val Gly Asp Phe His Tyr Val Ser Gly Met Thr
            180                 185                 190 act gac aat ctt aaa tgc ccg tgc cag atc cca tcg ccc gaa ttt ttc     624
Thr Asp Asn Leu Lys Cys Pro Cys Gln Ile Pro Ser Pro Glu Phe Phe
        195                 200                 205 aca gaa ttg gac ggg gtg cgc cta cac agg ttt gcg ccc cct tgc aag     672
Thr Glu Leu Asp Gly Val Arg Leu His Arg Phe Ala Pro Pro Cys Lys
```

-continued

| | | | | | | | | | | | | | | | | |
|---|---|---|---|---|---|---|---|---|---|---|---|---|---|---|---|---|
| | | 210 | | | | 215 | | | | | 220 | | | | | |
| ccc | ttg | ctg | cgg | gag | gag | gta | tca | ttc | aga | gta | gga | ctc | cac | gag | tac | 720 |
| Pro | Leu | Leu | Arg | Glu | Glu | Val | Ser | Phe | Arg | Val | Gly | Leu | His | Glu | Tyr | |
| 225 | | | | | 230 | | | | | 235 | | | | | 240 | |
| ccg | gtg | ggg | tcg | caa | tta | cct | tgc | gag | ccc | gaa | ccg | gac | gta | gcc | gtg | 768 |
| Pro | Val | Gly | Ser | Gln | Leu | Pro | Cys | Glu | Pro | Glu | Pro | Asp | Val | Ala | Val | |
| | | | | 245 | | | | | 250 | | | | | 255 | | |
| ttg | acg | tcc | atg | ctc | act | gat | ccc | tcc | cat | ata | aca | gca | gag | gcg | gcc | 816 |
| Leu | Thr | Ser | Met | Leu | Thr | Asp | Pro | Ser | His | Ile | Thr | Ala | Glu | Ala | Ala | |
| | | | 260 | | | | | 265 | | | | | 270 | | | |
| ggg | aga | agg | ttg | gcg | aga | ggg | tca | ccc | cct | tct | atg | gcc | agc | tcc | tcg | 864 |
| Gly | Arg | Arg | Leu | Ala | Arg | Gly | Ser | Pro | Pro | Ser | Met | Ala | Ser | Ser | Ser | |
| | | 275 | | | | | 280 | | | | | 285 | | | | |
| gct | agc | cag | ctg | tcc | gct | cca | tct | ctc | aag | gca | act | tgc | acc | gcc | aac | 912 |
| Ala | Ser | Gln | Leu | Ser | Ala | Pro | Ser | Leu | Lys | Ala | Thr | Cys | Thr | Ala | Asn | |
| | 290 | | | | | 295 | | | | | 300 | | | | | |
| cat | gac | tcc | cct | gac | gcc | gag | ctc | ata | gag | gct | aac | ctc | ctg | tgg | agg | 960 |
| His | Asp | Ser | Pro | Asp | Ala | Glu | Leu | Ile | Glu | Ala | Asn | Leu | Leu | Trp | Arg | |
| 305 | | | | | 310 | | | | | 315 | | | | | 320 | |
| cag | gag | atg | ggc | ggc | aac | atc | acc | agg | gtt | gag | tca | gag | aac | aaa | gtg | 1008 |
| Gln | Glu | Met | Gly | Gly | Asn | Ile | Thr | Arg | Val | Glu | Ser | Glu | Asn | Lys | Val | |
| | | | | 325 | | | | | 330 | | | | | 335 | | |
| gtg | att | ctg | gac | tcc | ttc | gat | ccg | ctt | gtg | gca | gag | gag | gat | gag | cgg | 1056 |
| Val | Ile | Leu | Asp | Ser | Phe | Asp | Pro | Leu | Val | Ala | Glu | Glu | Asp | Glu | Arg | |
| | | | | 340 | | | | | 345 | | | | | 350 | | |
| gag | gtc | tcc | gta | cct | gca | gaa | att | ctg | cgg | aag | tct | cgg | aga | ttc | gcc | 1104 |
| Glu | Val | Ser | Val | Pro | Ala | Glu | Ile | Leu | Arg | Lys | Ser | Arg | Arg | Phe | Ala | |
| | | 355 | | | | | 360 | | | | | 365 | | | | |
| cgg | gcc | ctg | ccc | gtc | tgg | gcg | cgg | ccg | gac | tac | aac | ccc | ccg | cta | gta | 1152 |
| Arg | Ala | Leu | Pro | Val | Trp | Ala | Arg | Pro | Asp | Tyr | Asn | Pro | Pro | Leu | Val | |
| | 370 | | | | | 375 | | | | | 380 | | | | | |
| gag | acg | tgg | aaa | aag | cct | gac | tac | gaa | cca | cct | gtg | gtc | cat | ggc | tgc | 1200 |
| Glu | Thr | Trp | Lys | Lys | Pro | Asp | Tyr | Glu | Pro | Pro | Val | Val | His | Gly | Cys | |
| 385 | | | | | 390 | | | | | 395 | | | | | 400 | |
| ccg | cta | cca | cct | cca | cgg | tcc | cct | cct | gtg | cct | ccg | cct | cgg | aaa | aag | 1248 |
| Pro | Leu | Pro | Pro | Pro | Arg | Ser | Pro | Pro | Val | Pro | Pro | Pro | Arg | Lys | Lys | |
| | | | | 405 | | | | | 410 | | | | | 415 | | |
| cgt | acg | gtg | gtc | ctc | acc | gaa | tca | acc | cta | tct | act | gcc | ttg | gcc | gag | 1296 |
| Arg | Thr | Val | Val | Leu | Thr | Glu | Ser | Thr | Leu | Ser | Thr | Ala | Leu | Ala | Glu | |
| | | | 420 | | | | | 425 | | | | | 430 | | | |
| ctt | gcc | acc | aaa | agt | ttt | ggc | agc | tcc | tca | act | tcc | ggc | att | acg | ggc | 1344 |
| Leu | Ala | Thr | Lys | Ser | Phe | Gly | Ser | Ser | Ser | Thr | Ser | Gly | Ile | Thr | Gly | |
| | | 435 | | | | | 440 | | | | | 445 | | | | |
| gac | aat | acg | aca | aca | tcc | tct | gag | ccc | gcc | cct | tct | ggc | tgc | ccc | ccc | 1392 |
| Asp | Asn | Thr | Thr | Thr | Ser | Ser | Glu | Pro | Ala | Pro | Ser | Gly | Cys | Pro | Pro | |
| | 450 | | | | | 455 | | | | | 460 | | | | | |
| gac | tcc | gac | gtt | gag | tcc | tat | tct | tcc | atg | ccc | ccc | ctg | gag | ggg | gag | 1440 |
| Asp | Ser | Asp | Val | Glu | Ser | Tyr | Ser | Ser | Met | Pro | Pro | Leu | Glu | Gly | Glu | |
| 465 | | | | | 470 | | | | | 475 | | | | | 480 | |
| cct | ggg | gat | ccg | gat | ctc | agc | gac | ggg | tca | tgg | tcg | acg | gtc | agt | agt | 1488 |
| Pro | Gly | Asp | Pro | Asp | Leu | Ser | Asp | Gly | Ser | Trp | Ser | Thr | Val | Ser | Ser | |
| | | | | 485 | | | | | 490 | | | | | 495 | | |
| ggg | gcc | gac | acg | gaa | gat | gtc | gtg | tgc | gga | cta | gtg | cgg | ccg | caa | ggc | 1536 |
| Gly | Ala | Asp | Thr | Glu | Asp | Val | Val | Cys | Gly | Leu | Val | Arg | Pro | Gln | Gly | |
| | | | 500 | | | | | 505 | | | | | 510 | | | |
| ggc | gga | tcc | gtg | gac | aag | aaa | att | gtg | ccc | agg | gat | tgt | ggt | tgt | aag | 1584 |
| Gly | Gly | Ser | Val | Asp | Lys | Lys | Ile | Val | Pro | Arg | Asp | Cys | Gly | Cys | Lys | |
| | | 515 | | | | | 520 | | | | | 525 | | | | |
| cct | tgc | ata | tgt | aca | gtc | cca | gaa | gta | tca | tct | gtc | ttc | atc | ttc | ccc | 1632 |
| Pro | Cys | Ile | Cys | Thr | Val | Pro | Glu | Val | Ser | Ser | Val | Phe | Ile | Phe | Pro | |

```
cca aag ccc aag gat gtg ctc acc att act ctg act cct aag gtc acg    1680
Pro Lys Pro Lys Asp Val Leu Thr Ile Thr Leu Thr Pro Lys Val Thr
545                 550                 555                 560 tgt gtt gtg gta gac atc agc aag gat gat ccc gag gtc cag ttc agc    1728
Cys Val Val Val Asp Ile Ser Lys Asp Asp Pro Glu Val Gln Phe Ser
                565                 570                 575 tgg ttt gta gat gat gtg gag gtg cac aca gct cag acg caa ccc cgg    1776
Trp Phe Val Asp Asp Val Glu Val His Thr Ala Gln Thr Gln Pro Arg
            580                 585                 590 gag gag cag ttc aac agc act ttc cgc tca gtc agt gaa ctt ccc atc    1824
Glu Glu Gln Phe Asn Ser Thr Phe Arg Ser Val Ser Glu Leu Pro Ile
        595                 600                 605 atg cac cag gac tgg ctc aat ggc aag gag ttc aaa tgc agg gtc aac    1872
Met His Gln Asp Trp Leu Asn Gly Lys Glu Phe Lys Cys Arg Val Asn
    610                 615                 620 agt gca gct ttc cct gcc ccc atc gag aaa acc atc tcc aaa acc aaa    1920
Ser Ala Ala Phe Pro Ala Pro Ile Glu Lys Thr Ile Ser Lys Thr Lys
625                 630                 635                 640 ggc aga ccg aag gct cca cag gtg tac acc att cca cct ccc aag gag    1968
Gly Arg Pro Lys Ala Pro Gln Val Tyr Thr Ile Pro Pro Pro Lys Glu
                645                 650                 655 cag atg gcc aag gat aaa gtc agt ctg acc tgc atg ata aca gac ttc    2016
Gln Met Ala Lys Asp Lys Val Ser Leu Thr Cys Met Ile Thr Asp Phe
            660                 665                 670 ttc cct gaa gac att act gtg gag tgg cag tgg aat ggg cag cca gcg    2064
Phe Pro Glu Asp Ile Thr Val Glu Trp Gln Trp Asn Gly Gln Pro Ala
        675                 680                 685 gag aac tac aag aac act cag ccc atc atg gac aca gat ggc tct tac    2112
Glu Asn Tyr Lys Asn Thr Gln Pro Ile Met Asp Thr Asp Gly Ser Tyr
    690                 695                 700 ttc gtc tac agc aag ctc aat gtg cag aag agc aac tgg gag gca gga    2160
Phe Val Tyr Ser Lys Leu Asn Val Gln Lys Ser Asn Trp Glu Ala Gly
705                 710                 715                 720 aat act ttc acc tgc tct gtg tta cat gag ggc ctg cac aac cac cat    2208
Asn Thr Phe Thr Cys Ser Val Leu His Glu Gly Leu His Asn His His
                725                 730                 735 act gag aag agc ctc tcc cac tct cct ggg ctg aat cta gag gaa act    2256
Thr Glu Lys Ser Leu Ser His Ser Pro Gly Leu Asn Leu Glu Glu Thr
            740                 745                 750 act gtt gtt aga cga cgg gac cga ggc agg tcc cct aga aga aga act    2304
Thr Val Val Arg Arg Arg Asp Arg Gly Arg Ser Pro Arg Arg Arg Thr
        755                 760                 765 ccc tcg cct cgc aga cgc aga tct caa tcg ccg cgt cgc aga aga tct    2352
Pro Ser Pro Arg Arg Arg Arg Ser Gln Ser Pro Arg Arg Arg Arg Ser
    770                 775                 780 caa tct cgg gaa tct caa tgt caa agc ttg tcg aga agt act aga gga    2400
Gln Ser Arg Glu Ser Gln Cys Gln Ser Leu Ser Arg Ser Thr Arg Gly
785                 790                 795                 800 tca taa                                                            2406
Ser

<210> SEQ ID NO 4
<211> LENGTH: 801
<212> TYPE: PRT
<213> ORGANISM: Hepatitis B virus

<400> SEQUENCE: 4

Met Val Ser Ala Ile Val Leu Tyr Val Leu Leu Ala Ala Ala His
1               5                   10                  15
```

```
Ser Ala Phe Ala Tyr Leu Gln Val Arg Ser Glu Thr Met Ser Tyr Tyr
            20                  25                  30

His His His His His His Asp Tyr Asp Ile Pro Thr Thr Glu Asn Leu
        35                  40                  45

Tyr Phe Gln Gly Ala Met Asp Pro Glu Phe Ser Gly Ser Trp Leu Arg
    50                  55                  60

Asp Ile Trp Asp Trp Ile Cys Glu Val Leu Ser Asp Phe Lys Thr Trp
65                  70                  75                  80

Leu Lys Ala Lys Leu Met Pro Gln Leu Pro Gly Ile Pro Phe Val Ser
                85                  90                  95

Cys Gln Arg Gly Tyr Arg Gly Val Trp Arg Gly Asp Gly Ile Met His
            100                 105                 110

Thr Arg Cys His Cys Gly Ala Glu Ile Thr Gly His Val Lys Asn Gly
        115                 120                 125

Thr Met Arg Ile Val Gly Pro Arg Thr Cys Arg Asn Met Trp Ser Gly
    130                 135                 140

Thr Phe Pro Ile Asn Ala Tyr Thr Thr Gly Pro Cys Thr Pro Leu Pro
145                 150                 155                 160

Ala Pro Asn Tyr Lys Phe Ala Leu Trp Arg Val Ser Ala Glu Glu Tyr
                165                 170                 175

Val Glu Ile Arg Arg Val Gly Asp Phe His Tyr Val Ser Gly Met Thr
            180                 185                 190

Thr Asp Asn Leu Lys Cys Pro Cys Gln Ile Pro Ser Pro Glu Phe Phe
        195                 200                 205

Thr Glu Leu Asp Gly Val Arg Leu His Arg Phe Ala Pro Pro Cys Lys
    210                 215                 220

Pro Leu Leu Arg Glu Glu Val Ser Phe Arg Val Gly Leu His Glu Tyr
225                 230                 235                 240

Pro Val Gly Ser Gln Leu Pro Cys Glu Pro Glu Pro Asp Val Ala Val
                245                 250                 255

Leu Thr Ser Met Leu Thr Asp Pro Ser His Ile Thr Ala Glu Ala Ala
            260                 265                 270

Gly Arg Arg Leu Ala Arg Gly Ser Pro Pro Ser Met Ala Ser Ser Ser
        275                 280                 285

Ala Ser Gln Leu Ser Ala Pro Ser Leu Lys Ala Thr Cys Thr Ala Asn
    290                 295                 300

His Asp Ser Pro Asp Ala Glu Leu Ile Glu Ala Asn Leu Leu Trp Arg
305                 310                 315                 320

Gln Glu Met Gly Gly Asn Ile Thr Arg Val Ser Glu Asn Lys Val
                325                 330                 335

Val Ile Leu Asp Ser Phe Asp Pro Leu Val Ala Glu Gly Asp Glu Arg
            340                 345                 350

Glu Val Ser Val Pro Ala Glu Ile Leu Arg Lys Ser Arg Arg Phe Ala
        355                 360                 365

Arg Ala Leu Pro Val Trp Ala Arg Pro Asp Tyr Asn Pro Pro Leu Val
    370                 375                 380

Glu Thr Trp Lys Lys Pro Asp Tyr Glu Pro Pro Val Val His Gly Cys
385                 390                 395                 400

Pro Leu Pro Pro Pro Arg Ser Pro Pro Val Pro Pro Pro Arg Lys Lys
                405                 410                 415

Arg Thr Val Val Leu Thr Glu Ser Thr Leu Ser Thr Ala Leu Ala Glu
            420                 425                 430

Leu Ala Thr Lys Ser Phe Gly Ser Ser Ser Thr Ser Gly Ile Thr Gly
        435                 440                 445
```

Asp Asn Thr Thr Thr Ser Ser Glu Pro Ala Pro Ser Gly Cys Pro Pro
    450                 455                 460

Asp Ser Asp Val Glu Ser Tyr Ser Ser Met Pro Pro Leu Glu Gly Glu
465                 470                 475                 480

Pro Gly Asp Pro Asp Leu Ser Asp Gly Ser Trp Ser Thr Val Ser Ser
                485                 490                 495

Gly Ala Asp Thr Glu Asp Val Val Cys Gly Leu Val Arg Pro Gln Gly
            500                 505                 510

Gly Gly Ser Val Asp Lys Lys Ile Val Pro Arg Asp Cys Gly Cys Lys
        515                 520                 525

Pro Cys Ile Cys Thr Val Pro Glu Val Ser Ser Val Phe Ile Phe Pro
    530                 535                 540

Pro Lys Pro Lys Asp Val Leu Thr Ile Thr Leu Thr Pro Lys Val Thr
545                 550                 555                 560

Cys Val Val Val Asp Ile Ser Lys Asp Asp Pro Glu Val Gln Phe Ser
                565                 570                 575

Trp Phe Val Asp Asp Val Glu Val His Thr Ala Gln Thr Gln Pro Arg
            580                 585                 590

Glu Glu Gln Phe Asn Ser Thr Phe Arg Ser Val Ser Glu Leu Pro Ile
        595                 600                 605

Met His Gln Asp Trp Leu Asn Gly Lys Glu Phe Lys Cys Arg Val Asn
    610                 615                 620

Ser Ala Ala Phe Pro Ala Pro Ile Glu Lys Thr Ile Ser Lys Thr Lys
625                 630                 635                 640

Gly Arg Pro Lys Ala Pro Gln Val Tyr Thr Ile Pro Pro Pro Lys Glu
                645                 650                 655

Gln Met Ala Lys Asp Lys Val Ser Leu Thr Cys Met Ile Thr Asp Phe
            660                 665                 670

Phe Pro Glu Asp Ile Thr Val Glu Trp Gln Trp Asn Gly Gln Pro Ala
        675                 680                 685

Glu Asn Tyr Lys Asn Thr Gln Pro Ile Met Asp Thr Asp Gly Ser Tyr
    690                 695                 700

Phe Val Tyr Ser Lys Leu Asn Val Gln Lys Ser Asn Trp Glu Ala Gly
705                 710                 715                 720

Asn Thr Phe Thr Cys Ser Val Leu His Glu Gly Leu His Asn His His
                725                 730                 735

Thr Glu Lys Ser Leu Ser His Ser Pro Gly Leu Asn Leu Glu Glu Thr
            740                 745                 750

Thr Val Val Arg Arg Arg Asp Arg Gly Arg Ser Pro Arg Arg Arg Thr
        755                 760                 765

Pro Ser Pro Arg Arg Arg Arg Ser Gln Ser Pro Arg Arg Arg Arg Ser
    770                 775                 780

Gln Ser Arg Glu Ser Gln Cys Gln Ser Leu Ser Arg Ser Thr Arg Gly
785                 790                 795                 800

Ser

<210> SEQ ID NO 5
<211> LENGTH: 2022
<212> TYPE: DNA
<213> ORGANISM: Hepatitis B virus
<220> FEATURE:
<221> NAME/KEY: CDS
<222> LOCATION: (1)..(2022)

<400> SEQUENCE: 5

```
atg gta agc gct att gtt tta tat gtg ctt ttg gcg gcg gcg cat        48
Met Val Ser Ala Ile Val Leu Tyr Val Leu Leu Ala Ala Ala His
1               5                   10                  15 tct gcc ttt gcg tat ctg cag gta cgg tcc gaa acc atg tcg tac tac    96
Ser Ala Phe Ala Tyr Leu Gln Val Arg Ser Glu Thr Met Ser Tyr Tyr
                20                  25                  30 cat cac cat cac cat cac gat tac gat atc cca acg acc gaa aac ctg   144
His His His His His His Asp Tyr Asp Ile Pro Thr Thr Glu Asn Leu
            35                  40                  45 tat ttt cag ggc gcc atg gat ccg gaa ttc aaa ggc cta cgt cga cga   192
Tyr Phe Gln Gly Ala Met Asp Pro Glu Phe Lys Gly Leu Arg Arg Arg
50                  55                  60 atg aaa aaa tgg tca tca aaa cct cgc aaa ggc atg ggg acg aat ctt   240
Met Lys Lys Trp Ser Ser Lys Pro Arg Lys Gly Met Gly Thr Asn Leu
65              70                  75                  80 tct gtt ccc aac cct ctg gga ttc ttt ccc gat cat cag ttg gac cct   288
Ser Val Pro Asn Pro Leu Gly Phe Phe Pro Asp His Gln Leu Asp Pro
                85                  90                  95 gta ttc gga gcc aac tca aac aat cca gat tgg gac ttc aac ccc atc   336
Val Phe Gly Ala Asn Ser Asn Asn Pro Asp Trp Asp Phe Asn Pro Ile
            100                 105                 110 aag gac cac tgg cca gca gcc aac cag gta gga gtg gga gca ttc ggg   384
Lys Asp His Trp Pro Ala Ala Asn Gln Val Gly Val Gly Ala Phe Gly
        115                 120                 125 cca ggg ttc acc cct cca cac ggc ggt gtt ttg ggg tgg agc cct cag   432
Pro Gly Phe Thr Pro Pro His Gly Gly Val Leu Gly Trp Ser Pro Gln
130                 135                 140 gct cag ggc atg ttg acc cca gtg tca aca att cct cct cct gcc tcc   480
Ala Gln Gly Met Leu Thr Pro Val Ser Thr Ile Pro Pro Pro Ala Ser
145                 150                 155                 160 gcc aat cgg cag tca gga agg cag cct act ccc atc tct cca cct cta   528
Ala Asn Arg Gln Ser Gly Arg Gln Pro Thr Pro Ile Ser Pro Pro Leu
                165                 170                 175 aga gac agt cat cct cag gcc atg cag tgg aat tcc act gcc ttc cac   576
Arg Asp Ser His Pro Gln Ala Met Gln Trp Asn Ser Thr Ala Phe His
            180                 185                 190 caa gct ctg caa gac ccc aga gtc agg ggt ctg tat ttt cct gct ggt   624
Gln Ala Leu Gln Asp Pro Arg Val Arg Gly Leu Tyr Phe Pro Ala Gly
        195                 200                 205 ggc tcc agt tca gga aca gta aac cct gct ccg aat att gcc tct cac   672
Gly Ser Ser Ser Gly Thr Val Asn Pro Ala Pro Asn Ile Ala Ser His
210                 215                 220 atc tcg tca atc tcc gcg agg acc ggg gac cct gtg acg aac atg gac   720
Ile Ser Ser Ile Ser Ala Arg Thr Gly Asp Pro Val Thr Asn Met Asp
225                 230                 235                 240 att gac cct tat aaa gaa ttt gga gct act gtg gag tta ctc tcg ttt   768
Ile Asp Pro Tyr Lys Glu Phe Gly Ala Thr Val Glu Leu Leu Ser Phe
                245                 250                 255 ttg cct tct gac ttc ttt cct tcc gtc aga gat ctc cta gac acc gcc   816
Leu Pro Ser Asp Phe Phe Pro Ser Val Arg Asp Leu Leu Asp Thr Ala
            260                 265                 270 tcg gct ctg tat cgg gaa gcc tta gag tct cct gag cat tgc tca cct   864
Ser Ala Leu Tyr Arg Glu Ala Leu Glu Ser Pro Glu His Cys Ser Pro
        275                 280                 285 cac cat acc gca ctc agg caa gcc att ctc tgc tgg ggg gaa ttg atg   912
His His Thr Ala Leu Arg Gln Ala Ile Leu Cys Trp Gly Glu Leu Met
290                 295                 300 act cta gct acc tgg gtg ggt aat aat ttg gaa gat cca gca tcc agg   960
Thr Leu Ala Thr Trp Val Gly Asn Asn Leu Glu Asp Pro Ala Ser Arg
305                 310                 315                 320
```

```
gat cta gta gtc aat tat gtt aat act aac atg gga tta aag atc agg      1008
Asp Leu Val Val Asn Tyr Val Asn Thr Asn Met Gly Leu Lys Ile Arg
            325                 330                 335 caa ctc ttg tgg ttt cat atc tct tgc ctt act ttt gga aga gaa act      1056
Gln Leu Leu Trp Phe His Ile Ser Cys Leu Thr Phe Gly Arg Glu Thr
        340                 345                 350 gta ctt gaa tat ttg gtc tct ttc gga gtg tgg att cgc act cct cca      1104
Val Leu Glu Tyr Leu Val Ser Phe Gly Val Trp Ile Arg Thr Pro Pro
    355                 360                 365 gcc tat aga cca cca aat gcc cct atc tta tca aca ctt ccg gaa act      1152
Ala Tyr Arg Pro Pro Asn Ala Pro Ile Leu Ser Thr Leu Pro Glu Thr
370                 375                 380 act gtt gtt aga cga cgg gac cga ggc agg tcc cct aga aga aga act      1200
Thr Val Val Arg Arg Arg Asp Arg Gly Arg Ser Pro Arg Arg Arg Thr
385                 390                 395                 400 ccc tcg cct cgc aga cgc aga tct caa tcg ccg cgt cgc aga aga tct      1248
Pro Ser Pro Arg Arg Arg Arg Ser Gln Ser Pro Arg Arg Arg Arg Ser
            405                 410                 415 caa tct cgg gaa tct caa tgt gtg cgg ccg caa ggc ggc gga tcc gtg      1296
Gln Ser Arg Glu Ser Gln Cys Val Arg Pro Gln Gly Gly Gly Ser Val
        420                 425                 430 gac aag aaa att gtg ccc gcg gat tgt ggt tgt gcg cct tgc ata tgt      1344
Asp Lys Lys Ile Val Pro Ala Asp Cys Gly Cys Ala Pro Cys Ile Cys
    435                 440                 445 gca gtc cca gaa gta tca tct gtc ttc atc ttc ccc cca aag ccc aag      1392
Ala Val Pro Glu Val Ser Ser Val Phe Ile Phe Pro Pro Lys Pro Lys
450                 455                 460 gat gtg ctc acc att act ctg act cct aag gtc acg tgt gtt gtg gta      1440
Asp Val Leu Thr Ile Thr Leu Thr Pro Lys Val Thr Cys Val Val Val
465                 470                 475                 480 gac atc agc aag gat gat ccc gag gtc cag ttc agc tgg ttt gta gat      1488
Asp Ile Ser Lys Asp Asp Pro Glu Val Gln Phe Ser Trp Phe Val Asp
            485                 490                 495 gat gtg gag gtg cac aca gct cag acg caa ccc cgg gag gag cag ttc      1536
Asp Val Glu Val His Thr Ala Gln Thr Gln Pro Arg Glu Glu Gln Phe
        500                 505                 510 aac agc act ttc cgc tca gtc agt gaa ctt ccc atc atg cac cag gac      1584
Asn Ser Thr Phe Arg Ser Val Ser Glu Leu Pro Ile Met His Gln Asp
    515                 520                 525 tgg ctc aat ggc aag gag ttc aaa tgc agg gtc aac agt gca gct ttc      1632
Trp Leu Asn Gly Lys Glu Phe Lys Cys Arg Val Asn Ser Ala Ala Phe
530                 535                 540 cct gcc ccc atc gag aaa acc atc tcc aaa acc aaa ggc aga ccg aag      1680
Pro Ala Pro Ile Glu Lys Thr Ile Ser Lys Thr Lys Gly Arg Pro Lys
545                 550                 555                 560 gct cca cag gtg tac acc att cca cct ccc aag gag cag atg gcc aag      1728
Ala Pro Gln Val Tyr Thr Ile Pro Pro Pro Lys Glu Gln Met Ala Lys
            565                 570                 575 gat aaa gtc agt ctg acc tgc atg ata aca gac ttc ttc cct gaa gac      1776
Asp Lys Val Ser Leu Thr Cys Met Ile Thr Asp Phe Phe Pro Glu Asp
        580                 585                 590 att act gtg gag tgg cag tgg aat ggg cag cca gcg gag aac tac aag      1824
Ile Thr Val Glu Trp Gln Trp Asn Gly Gln Pro Ala Glu Asn Tyr Lys
    595                 600                 605 aac act cag ccc atc atg gac aca gat ggc tct tac ttc gtc tac agc      1872
Asn Thr Gln Pro Ile Met Asp Thr Asp Gly Ser Tyr Phe Val Tyr Ser
610                 615                 620 aag ctc aat gtg cag aag agc aac tgg gag gca gga aat act ttc acc      1920
Lys Leu Asn Val Gln Lys Ser Asn Trp Glu Ala Gly Asn Thr Phe Thr
625                 630                 635                 640
```

-continued

```
tgc tct gtg tta cat gag ggc ctg cac aac cac cat act gag aag agc    1968
Cys Ser Val Leu His Glu Gly Leu His Asn His His Thr Glu Lys Ser
            645                 650                 655 ctc tcc cac tct cct ggg ctg caa agc ttg tcg aga agt act aga gga    2016
Leu Ser His Ser Pro Gly Leu Gln Ser Leu Ser Arg Ser Thr Arg Gly
            660                 665                 670 tca taa                                                             2022
Ser
```

<210> SEQ ID NO 6
<211> LENGTH: 673
<212> TYPE: PRT
<213> ORGANISM: Hepatitis B virus

<400> SEQUENCE: 6

```
Met Val Ser Ala Ile Val Leu Tyr Val Leu Leu Ala Ala Ala Ala His
1               5                   10                  15

Ser Ala Phe Ala Tyr Leu Gln Val Arg Ser Glu Thr Met Ser Tyr Tyr
                20                  25                  30

His His His His His His Asp Tyr Asp Ile Pro Thr Thr Glu Asn Leu
            35                  40                  45

Tyr Phe Gln Gly Ala Met Asp Pro Glu Phe Lys Gly Leu Arg Arg Arg
    50                  55                  60

Met Lys Lys Trp Ser Ser Lys Pro Arg Lys Gly Met Gly Thr Asn Leu
65                  70                  75                  80

Ser Val Pro Asn Pro Leu Gly Phe Phe Pro Asp His Gln Leu Asp Pro
                85                  90                  95

Val Phe Gly Ala Asn Ser Asn Asn Pro Asp Trp Asp Phe Asn Pro Ile
            100                 105                 110

Lys Asp His Trp Pro Ala Ala Asn Gln Val Gly Val Gly Ala Phe Gly
        115                 120                 125

Pro Gly Phe Thr Pro Pro His Gly Gly Val Leu Gly Trp Ser Pro Gln
    130                 135                 140

Ala Gln Gly Met Leu Thr Pro Val Ser Thr Ile Pro Pro Pro Ala Ser
145                 150                 155                 160

Ala Asn Arg Gln Ser Gly Arg Gln Pro Thr Pro Ile Ser Pro Pro Leu
                165                 170                 175

Arg Asp Ser His Pro Gln Ala Met Gln Trp Asn Ser Thr Ala Phe His
            180                 185                 190

Gln Ala Leu Gln Asp Pro Arg Val Arg Gly Leu Tyr Phe Pro Ala Gly
        195                 200                 205

Gly Ser Ser Ser Gly Thr Val Asn Pro Ala Pro Asn Ile Ala Ser His
    210                 215                 220

Ile Ser Ser Ile Ser Ala Arg Thr Gly Asp Pro Val Thr Asn Met Asp
225                 230                 235                 240

Ile Asp Pro Tyr Lys Glu Phe Gly Ala Thr Val Glu Leu Leu Ser Phe
                245                 250                 255

Leu Pro Ser Asp Phe Phe Pro Ser Val Arg Asp Leu Leu Asp Thr Ala
            260                 265                 270

Ser Ala Leu Tyr Arg Glu Ala Leu Glu Ser Pro Glu His Cys Ser Pro
        275                 280                 285

His His Thr Ala Leu Arg Gln Ala Ile Leu Cys Trp Gly Glu Leu Met
    290                 295                 300

Thr Leu Ala Thr Trp Val Gly Asn Asn Leu Glu Asp Pro Ala Ser Arg
305                 310                 315                 320

Asp Leu Val Val Asn Tyr Val Asn Thr Asn Met Gly Leu Lys Ile Arg
```

```
                      325                 330                 335
Gln Leu Leu Trp Phe His Ile Ser Cys Leu Thr Phe Gly Arg Glu Thr
                340                 345                 350

Val Leu Glu Tyr Leu Val Ser Phe Gly Val Trp Ile Arg Thr Pro Pro
            355                 360                 365

Ala Tyr Arg Pro Pro Asn Ala Pro Ile Leu Ser Thr Leu Pro Glu Thr
        370                 375                 380

Thr Val Val Arg Arg Arg Asp Arg Gly Arg Ser Pro Arg Arg Arg Thr
385                 390                 395                 400

Pro Ser Pro Arg Arg Arg Arg Ser Gln Ser Pro Arg Arg Arg Arg Ser
                405                 410                 415

Gln Ser Arg Glu Ser Gln Cys Val Arg Pro Gln Gly Gly Gly Ser Val
            420                 425                 430

Asp Lys Lys Ile Val Pro Ala Asp Cys Gly Cys Ala Pro Cys Ile Cys
        435                 440                 445

Ala Val Pro Glu Val Ser Ser Val Phe Ile Phe Pro Pro Lys Pro Lys
    450                 455                 460

Asp Val Leu Thr Ile Thr Leu Thr Pro Lys Val Thr Cys Val Val Val
465                 470                 475                 480

Asp Ile Ser Lys Asp Asp Pro Glu Val Gln Phe Ser Trp Phe Val Asp
                485                 490                 495

Asp Val Glu Val His Thr Ala Gln Thr Gln Pro Arg Glu Glu Gln Phe
            500                 505                 510

Asn Ser Thr Phe Arg Ser Val Ser Glu Leu Pro Ile Met His Gln Asp
        515                 520                 525

Trp Leu Asn Gly Lys Glu Phe Lys Cys Arg Val Asn Ser Ala Ala Phe
    530                 535                 540

Pro Ala Pro Ile Glu Lys Thr Ile Ser Lys Thr Lys Gly Arg Pro Lys
545                 550                 555                 560

Ala Pro Gln Val Tyr Thr Ile Pro Pro Lys Glu Gln Met Ala Lys
                565                 570                 575

Asp Lys Val Ser Leu Thr Cys Met Ile Thr Asp Phe Phe Pro Glu Asp
            580                 585                 590

Ile Thr Val Glu Trp Gln Trp Asn Gly Gln Pro Ala Glu Asn Tyr Lys
        595                 600                 605

Asn Thr Gln Pro Ile Met Asp Thr Asp Gly Ser Tyr Phe Val Tyr Ser
    610                 615                 620

Lys Leu Asn Val Gln Lys Ser Asn Trp Glu Ala Gly Asn Thr Phe Thr
625                 630                 635                 640

Cys Ser Val Leu His Glu Gly Leu His Asn His His Thr Glu Lys Ser
                645                 650                 655

Leu Ser His Ser Pro Gly Leu Gln Ser Leu Ser Arg Ser Thr Arg Gly
            660                 665                 670

Ser

<210> SEQ ID NO 7
<211> LENGTH: 41
<212> TYPE: PRT
<213> ORGANISM: Hepatitis B virus

<400> SEQUENCE: 7

Glu Thr Thr Val Val Arg Arg Arg Asp Arg Gly Arg Ser Pro Arg Arg
1               5                   10                  15

Arg Thr Pro Ser Pro Arg Arg Arg Arg Ser Gln Ser Pro Arg Arg Arg
            20                  25                  30
```

Arg Ser Gln Ser Arg Glu Ser Gln Cys
        35                  40

<210> SEQ ID NO 8
<211> LENGTH: 56
<212> TYPE: DNA
<213> ORGANISM: Artificial Sequence
<220> FEATURE:
<223> OTHER INFORMATION: Synthetic primer

<400> SEQUENCE: 8
tgtcattctg cggccgcaag gcggcgggat ccgtggacaa gaaaattgtg cccagg    56

<210> SEQ ID NO 9
<211> LENGTH: 33
<212> TYPE: DNA
<213> ORGANISM: Artificial Sequence
<220> FEATURE:
<223> OTHER INFORMATION: Synthetic primer

<400> SEQUENCE: 9
ccggtctaga ttcagcccag gagagtggga gag    33

<210> SEQ ID NO 10
<211> LENGTH: 33
<212> TYPE: DNA
<213> ORGANISM: Artificial Sequence
<220> FEATURE:
<223> OTHER INFORMATION: Synthetic primer

<400> SEQUENCE: 10
ccggtctaga ggaaactact gttgttagac gac    33

<210> SEQ ID NO 11
<211> LENGTH: 33
<212> TYPE: DNA
<213> ORGANISM: Artificial Sequence
<220> FEATURE:
<223> OTHER INFORMATION: Synthetic primer

<400> SEQUENCE: 11
gcgcaagctt tgacattgag attcccgaga ttg    33

<210> SEQ ID NO 12
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 12
gcauccgcgu gcacuuuca    19

<210> SEQ ID NO 13
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 13
gguggcagcc gacaaugca    19

<210> SEQ ID NO 14
<211> LENGTH: 19
<212> TYPE: RNA

```
<213> ORGANISM: Artificial Sequence
<220> FEATURE:
<223> OTHER INFORMATION: Synthetic oligonucleotide

<400> SEQUENCE: 14
ggacgccugc ggauucuac                                              19

<210> SEQ ID NO 15
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 15
uguuauuacu ugccuggaa                                              19

<210> SEQ ID NO 16
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 16
gacacgcacu uccgcacauu u                                           21

<210> SEQ ID NO 17
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 17
gcauccgcgu gcacuuucau u                                           21

<210> SEQ ID NO 18
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 18
gguggcagcc gacaaugcau u                                           21

<210> SEQ ID NO 19
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 19
ggacgccugc ggauucuacu u                                           21
```